(12) United States Patent
Koska et al.

(10) Patent No.: US 12,336,959 B2
(45) Date of Patent: *Jun. 24, 2025

(54) SYSTEMS AND METHODS FOR FLUID DELIVERY MANIFOLDS

(71) Applicant: Koska Family Limited, Eastbourne (GB)

(72) Inventors: Marc Andrew Koska, Dartmouth (GB); Jay S. Walker, Ridgefield, CT (US)

(73) Assignee: Koska Family Limited, East Sussex (GB)

( * ) Notice: Subject to any disclaimer, the term of this patent is extended or adjusted under 35 U.S.C. 154(b) by 104 days.

This patent is subject to a terminal disclaimer.

(21) Appl. No.: 18/181,664

(22) Filed: Mar. 10, 2023

(65) Prior Publication Data
US 2023/0210720 A1 Jul. 6, 2023

Related U.S. Application Data

(63) Continuation of application No. 16/876,417, filed on May 18, 2020, now Pat. No. 11,607,369, which is a
(Continued)

(51) Int. Cl.
*A61J 1/06* (2006.01)
*A61M 5/00* (2006.01)
(Continued)

(52) U.S. Cl.
CPC .............. *A61J 1/067* (2013.01); *A61M 5/002* (2013.01); *A61M 5/288* (2013.01);
(Continued)

(58) Field of Classification Search
CPC ........ A61J 1/067; A61M 5/002; A61M 5/288; A61M 2205/52
See application file for complete search history.

(56) References Cited

U.S. PATENT DOCUMENTS

| | | |
|---|---|---|
| 2,667,165 A | 1/1954 | Smith |
| 2,717,598 A | 9/1955 | Krasno |

(Continued)

FOREIGN PATENT DOCUMENTS

| | | |
|---|---|---|
| AU | 2337470 | 6/1972 |
| AU | 2019203408 B2 | 9/2020 |

(Continued)

OTHER PUBLICATIONS

Office Action for Australian Application 2017256152 dated Nov. 12, 2021; 4 pps.

(Continued)

*Primary Examiner* — Bradley J Osinski
(74) *Attorney, Agent, or Firm* — RowanTree Law Group, PLLC; Carson C. K. Fincham

(57) ABSTRACT

A fluid delivery manifold system assembled and configured to allow delivery of a single dose of a therapeutic agent (e.g., vaccine, drug, medicament, etc.) from a Blow-Fill-Seal (BFS) vial to a patient. The delivery assembly generally includes a modular manifold design consisting of separately constructed components cooperatively arranged and coupled to one another. The modular manifold construction allows for rapid manufacturing reconfigurations of one or more components with minimal costs to create new delivery manifold configurations that meet specific needs (i.e., different modes of delivery depending on agent to be delivered, such as subcutaneous, intramuscular, intradermal, intravenous injection, spray, or droplet delivery).

20 Claims, 6 Drawing Sheets

Related U.S. Application Data continuation of application No. PCT/US2018/061696, filed on Nov. 16, 2018.

(60) Provisional application No. 62/680,116, filed on Jun. 4, 2018, provisional application No. 62/674,565, filed on May 21, 2018, provisional application No. 62/587,879, filed on Nov. 17, 2017.

(51) Int. Cl.
*A61M 5/28* (2006.01)
*A61M 5/32* (2006.01)

(52) U.S. Cl.
CPC ........ *A61M 5/3202* (2013.01); *A61J 2200/72* (2013.01); *A61J 2205/20* (2013.01); *A61J 2205/30* (2013.01); *A61M 2202/30* (2013.01); *A61M 2205/3546* (2013.01); *A61M 2205/52* (2013.01)

(56) References Cited

U.S. PATENT DOCUMENTS

| | | |
|---|---|---|
| 2,828,743 A | 4/1958 | Ashkenaz |
| 3,073,307 A | 1/1963 | Stevens |
| 3,192,925 A | 7/1965 | James |
| 3,251,915 A | 5/1966 | Pechthold |
| 3,406,686 A | 10/1968 | Keller |
| 3,491,757 A | 1/1970 | Arce |
| 3,640,388 A | 2/1972 | Ferrari |
| 3,917,120 A | 11/1975 | Larenz |
| 3,989,045 A | 11/1976 | Van Eck |
| 4,018,222 A | 4/1977 | McAleer |
| 4,022,206 A | 5/1977 | Hilleman |
| 4,130,117 A | 12/1978 | Van Eck |
| 4,502,616 A | 3/1985 | Meierhoefer |
| 4,539,172 A | 9/1985 | Winchell |
| 4,643,309 A | 2/1987 | Evers |
| 4,671,763 A | 6/1987 | Weiler |
| 4,883,473 A | 11/1989 | Thomas |
| 4,955,871 A | 9/1990 | Thomas |
| 4,966,581 A | 10/1990 | Landau |
| 4,979,630 A | 12/1990 | Rose |
| 4,995,519 A | 2/1991 | Rose |
| 5,112,311 A | 5/1992 | Utterberg |
| 5,135,514 A | 8/1992 | Kimber |
| 5,139,489 A | 8/1992 | Hollister |
| 5,217,480 A | 6/1993 | Haber |
| 5,222,948 A | 6/1993 | Austin |
| 5,242,422 A | 9/1993 | Schneberger |
| 5,261,881 A | 11/1993 | Riner |
| 5,356,052 A | 10/1994 | Poynter |
| 5,370,626 A | 12/1994 | Farris |
| 5,374,263 A | 12/1994 | Weiler |
| 5,395,365 A | 3/1995 | Weiler |
| 5,409,125 A | 4/1995 | Kimber |
| 5,427,275 A | 6/1995 | Hansen |
| 5,503,885 A | 4/1996 | Anderson |
| 5,509,906 A | 4/1996 | Poynter |
| 5,533,505 A | 7/1996 | Kaellstrand |
| 5,624,407 A | 4/1997 | Claro |
| 5,636,640 A | 6/1997 | Staehlin |
| 5,761,885 A | 6/1998 | Hansen |
| 5,944,699 A | 8/1999 | Barrelle |
| 6,050,400 A | 4/2000 | Taskis |
| D425,617 S | 5/2000 | Snedden |
| 6,065,270 A | 5/2000 | Reinhard |
| 6,068,148 A | 5/2000 | Weiler |
| 6,120,478 A | 9/2000 | Moore |
| 6,134,866 A | 10/2000 | Schoenewolff |
| 6,173,852 B1 | 1/2001 | Browne |
| 6,200,296 B1 | 3/2001 | Dibiasi |
| 6,231,559 B1 | 5/2001 | Loretti |
| 6,241,124 B1 | 6/2001 | Hoyt |
| 6,258,063 B1 | 7/2001 | Haar |
| D447,560 S | 9/2001 | Hellberg |
| 6,332,876 B1 | 12/2001 | Poynter |
| 6,357,626 B1 | 3/2002 | Zhang |
| 6,379,342 B1 | 4/2002 | Levinson |
| 6,383,166 B1 | 5/2002 | Farris |
| D458,366 S | 6/2002 | Hellberg |
| D462,760 S | 9/2002 | Ahlgrim |
| D467,336 S | 12/2002 | Gilbard |
| 6,517,768 B1 | 2/2003 | Weiler |
| D471,628 S | 3/2003 | Louviere |
| 6,585,134 B2 | 7/2003 | Farris |
| 6,626,308 B2 | 9/2003 | Weiler |
| D492,407 S | 6/2004 | Masuda |
| 6,764,463 B1 | 7/2004 | Farris |
| 6,777,052 B2 | 8/2004 | Kai |
| 6,860,405 B1 | 3/2005 | Poynter |
| 6,918,418 B1 | 7/2005 | Farris |
| D517,207 S | 3/2006 | Poynter |
| 7,028,862 B2 | 4/2006 | Poynter |
| 7,029,465 B2 | 4/2006 | Heyes |
| 7,100,600 B2 | 9/2006 | Loeffler |
| 7,188,750 B2 | 3/2007 | Vogel |
| 7,308,782 B2 | 12/2007 | Hansen |
| 7,357,893 B2 | 4/2008 | Hansen |
| D573,710 S | 7/2008 | Goodman |
| 7,425,207 B2 | 9/2008 | Miller |
| 7,438,704 B1 | 10/2008 | Kawashima |
| 7,487,894 B2 | 2/2009 | Zahn |
| 7,513,397 B2 | 4/2009 | Zahn |
| 7,562,796 B2 | 7/2009 | Zahn |
| 7,632,253 B2 | 12/2009 | Ooyauchi |
| D618,339 S | 6/2010 | Hansen |
| 7,832,594 B2 | 11/2010 | Yamada |
| 7,832,601 B2 | 11/2010 | Zahn |
| 7,866,514 B1 | 1/2011 | Hansen |
| 7,883,660 B2 | 2/2011 | Matsuda |
| 7,892,211 B2 | 2/2011 | McCulloch |
| 7,892,614 B2 | 2/2011 | Radermacher |
| 7,993,304 B2 | 8/2011 | Kriesel |
| 8,087,524 B2 | 1/2012 | Hansen |
| 8,133,202 B2 | 3/2012 | Marsh |
| D674,481 S | 1/2013 | Decoste |
| 8,377,029 B2 | 2/2013 | Nagao |
| D681,196 S | 4/2013 | Henrikson |
| 8,431,068 B2 | 4/2013 | Hansen |
| 8,434,643 B2 | 5/2013 | Harris |
| 8,464,918 B1 | 6/2013 | Harris |
| 8,486,043 B2 | 7/2013 | Iyer |
| 8,486,501 B2 | 7/2013 | Manabe |
| 8,551,053 B2 | 10/2013 | Hansen |
| 8,640,873 B2 | 2/2014 | Nakano |
| 8,652,096 B2 | 2/2014 | Alvey |
| 8,663,188 B2 | 3/2014 | Genosar |
| 8,672,885 B2 | 3/2014 | Kriesel |
| D710,993 S | 8/2014 | Decoste |
| 8,795,226 B2 | 8/2014 | Kuhn |
| 8,857,470 B2 | 10/2014 | Rahimy |
| D721,434 S | 1/2015 | Mulvey |
| 8,967,140 B2 | 3/2015 | Denyer |
| 8,986,236 B2 | 3/2015 | Slokovic |
| D731,642 S | 6/2015 | Cehajic |
| 9,079,686 B2 | 7/2015 | Domkowski |
| 9,095,500 B2 | 8/2015 | Brandenburger |
| 9,108,777 B1 | 8/2015 | Santamarta |
| 9,132,238 B2 | 9/2015 | Ferreri |
| 9,150,317 B2 | 10/2015 | Hansen |
| 9,168,201 B2 | 10/2015 | McAffer |
| 9,216,477 B2 | 12/2015 | Gibson |
| 9,242,051 B2 | 1/2016 | Jugl |
| 9,248,076 B2 | 2/2016 | Sullivan |
| 9,265,889 B2 | 2/2016 | Thornton |
| D753,292 S | 4/2016 | Oates, II |
| 9,314,403 B2 | 4/2016 | Smith |
| 9,358,738 B2 | 6/2016 | Wolters |
| 9,364,393 B1 | 6/2016 | Grabowski |
| 9,399,102 B2 | 7/2016 | Dewoolfson |
| 9,526,839 B2 | 12/2016 | Chia |
| D776,266 S | 1/2017 | Dombrowski |
| 9,533,065 B2 | 1/2017 | Foreman |

(56) References Cited

U.S. PATENT DOCUMENTS

| | | |
|---|---|---|
| D779,653 S | 2/2017 | Habig |
| 9,592,354 B2 | 3/2017 | Sullivan |
| 9,597,259 B2 | 3/2017 | Becker |
| 9,737,664 B2 | 8/2017 | Gardner |
| 9,808,608 B2 | 11/2017 | Webb |
| 9,820,913 B2 | 11/2017 | Genosar |
| 9,828,148 B2 | 11/2017 | Schreckenhoefer |
| 9,908,682 B2 | 3/2018 | McAffer |
| 9,918,900 B2 | 3/2018 | Hansen |
| 9,987,790 B2 | 6/2018 | Suyama |
| 10,018,536 B2 | 7/2018 | Huschke |
| 10,039,884 B2 | 8/2018 | Ferreri |
| 10,064,785 B2 | 9/2018 | Spallek |
| 10,086,984 B2 | 10/2018 | Colangelo |
| 10,098,814 B2 | 10/2018 | Spallek |
| 10,105,491 B2 | 10/2018 | Gelblum |
| 10,117,994 B2 | 11/2018 | Holtwick |
| 10,118,000 B2 | 11/2018 | Schraga |
| 10,147,268 B2 | 12/2018 | Walker |
| 10,149,939 B2 | 12/2018 | Giambattista |
| 10,155,088 B2 | 12/2018 | Basile |
| 10,155,829 B2 | 12/2018 | Destro |
| 10,207,053 B2 | 2/2019 | Groskopf |
| 10,278,896 B2 | 5/2019 | Brandenburger |
| 10,315,788 B2 | 6/2019 | Consolaro |
| 10,335,507 B2 | 7/2019 | Reed |
| 10,342,735 B2 | 7/2019 | Chou |
| 10,351,272 B2 | 7/2019 | Colangelo |
| 10,363,369 B2 | 7/2019 | Cosman |
| D859,647 S | 9/2019 | Chang |
| 10,456,328 B2 | 10/2019 | Brandenburger |
| 10,464,708 B2 | 11/2019 | Geser |
| 10,471,244 B2 | 11/2019 | Dombrowski |
| 10,500,338 B2 | 12/2019 | Berenshteyn |
| 10,512,591 B2 | 12/2019 | Oshgan |
| 10,525,212 B2 | 1/2020 | Thornton |
| 10,543,317 B2 | 1/2020 | Basile |
| 10,543,944 B2 | 1/2020 | Batema |
| 10,583,256 B2 | 3/2020 | Berry |
| 10,589,075 B2 | 3/2020 | Wills |
| 10,639,839 B2 | 5/2020 | Consolaro |
| 10,716,901 B2 | 7/2020 | Genosar |
| 10,737,840 B2 | 8/2020 | Oates, II |
| 10,765,849 B2 | 9/2020 | Chiang |
| D898,901 S | 10/2020 | De Malibran-Santibanez |
| 10,793,323 B2 | 10/2020 | Cosman |
| 10,821,053 B2 | 11/2020 | Rajagopal |
| 10,828,860 B2 | 11/2020 | Vaes |
| 10,874,588 B2 | 12/2020 | Schabbach |
| 10,888,454 B2 | 1/2021 | Ivri |
| 10,918,809 B2 | 2/2021 | Ferreri |
| 10,928,236 B2 | 2/2021 | Adler |
| 10,933,190 B2 | 3/2021 | Berry |
| 10,940,633 B2 | 3/2021 | Schubert |
| 10,961,003 B2 | 3/2021 | Banuelos |
| 10,967,126 B2 | 4/2021 | Holtwick |
| 10,981,713 B2 | 4/2021 | Genosar |
| 11,027,862 B2 | 6/2021 | Wong |
| 11,059,638 B2 | 7/2021 | Spallek |
| 11,077,263 B2 | 8/2021 | Loenner |
| 11,123,499 B2 | 9/2021 | Basile |
| 11,136,148 B2 | 10/2021 | Rehbein |
| 11,167,889 B2 | 11/2021 | Ikeda |
| 11,173,022 B2 | 11/2021 | De Malibran-Santibanez |
| 11,185,634 B2 | 11/2021 | Genosar |
| 11,191,910 B2 | 12/2021 | Hoekman |
| 11,198,243 B2 | 12/2021 | Beck |
| D943,092 S | 2/2022 | Buehrle |
| 11,279,098 B2 | 3/2022 | Groh |
| 11,285,504 B2 | 3/2022 | Wilkerson |
| D952,137 S | 5/2022 | Chandrapati |
| 11,324,660 B2 | 5/2022 | Geser |
| D954,943 S | 6/2022 | Byron |
| 11,351,090 B2 | 6/2022 | Brandenburger |
| 11,351,715 B2 | 6/2022 | Sauter |
| 11,353,406 B2 | 6/2022 | Prinz |
| 11,377,263 B2 | 7/2022 | Gydesen |
| 11,382,833 B2 | 7/2022 | Koska |
| 11,396,123 B2 | 7/2022 | Hoshino |
| 11,400,241 B2 | 8/2022 | Patton |
| 11,400,637 B2 | 8/2022 | Shiokawa |
| 11,400,638 B2 | 8/2022 | Hoshino |
| 11,419,984 B2 | 8/2022 | Schabbach |
| 11,446,209 B2 | 9/2022 | Barkman |
| 11,446,856 B2 | 9/2022 | Furlotti |
| 11,534,551 B2 | 12/2022 | Ferreri |
| 11,565,838 B2 | 1/2023 | Meier |
| 11,591,126 B2 | 2/2023 | Köppel et al. |
| 11,607,369 B2 | 3/2023 | Koska |
| 11,638,783 B2 | 5/2023 | Consolaro |
| 11,648,180 B2 | 5/2023 | Genosar |
| D992,110 S | 7/2023 | Price |
| 2002/0104856 A1 | 8/2002 | Clark |
| 2003/0050602 A1 | 3/2003 | Pettis |
| 2003/0186456 A1 | 10/2003 | Stroup |
| 2004/0015131 A1 | 1/2004 | Flaherty |
| 2004/0118477 A1 | 6/2004 | Desmond |
| 2005/0049560 A1 | 3/2005 | Hauri |
| 2006/0032189 A1 | 2/2006 | Giacobbe |
| 2006/0073173 A1 | 4/2006 | Banach |
| 2006/0108385 A1 | 5/2006 | Zahn |
| 2007/0167904 A1 | 7/2007 | Zinger |
| 2007/0191780 A1 | 8/2007 | Modi |
| 2007/0260188 A1 | 11/2007 | Kelly |
| 2008/0000798 A1 | 1/2008 | Gutmann |
| 2008/0083691 A1 | 4/2008 | Poynter |
| 2008/0228162 A1 | 9/2008 | Trager |
| 2008/0243077 A1 | 10/2008 | Bivin |
| 2008/0258334 A1 | 10/2008 | Hansen |
| 2008/0262466 A1 | 10/2008 | Smith |
| 2009/0025823 A1 | 1/2009 | Hansen |
| 2009/0171311 A1 | 7/2009 | Genosar |
| 2009/0216212 A1 | 8/2009 | Fangrow, Jr. |
| 2009/0230077 A1 | 9/2009 | Poynter |
| 2009/0230080 A1 | 9/2009 | Hansen |
| 2010/0163577 A1 | 7/2010 | Hansen |
| 2010/0249716 A1 | 9/2010 | Wong |
| 2011/0031157 A1 | 2/2011 | Nakano |
| 2011/0131929 A1 | 6/2011 | McAffer |
| 2011/0135720 A1 | 6/2011 | Seabrook, Jr. |
| 2011/0160677 A1 | 6/2011 | March |
| 2011/0186451 A1 | 8/2011 | Pontus |
| 2011/0224640 A1 | 9/2011 | Bernd |
| 2012/0027818 A1 | 2/2012 | Glausch |
| 2012/0074001 A1 | 3/2012 | Amir |
| 2012/0083744 A1 | 4/2012 | Finke |
| 2012/0179109 A1 | 7/2012 | Takemoto |
| 2012/0238962 A1 | 9/2012 | Chin |
| 2013/0015204 A1 | 1/2013 | Gol |
| 2013/0098864 A1 | 4/2013 | Fontana |
| 2013/0104324 A1 | 5/2013 | Greer, Jr. |
| 2013/0110053 A1 | 5/2013 | Yoshino |
| 2013/0345672 A1 | 12/2013 | Ferreri |
| 2013/0345673 A1 | 12/2013 | Ferreri |
| 2014/0008366 A1 | 1/2014 | Genosar |
| 2014/0039444 A1 | 2/2014 | Akihito |
| 2014/0046270 A1 | 2/2014 | Thornton |
| 2014/0054295 A1 | 2/2014 | Holtwick |
| 2014/0069839 A1 | 3/2014 | Colin |
| 2014/0188502 A1 | 7/2014 | Defrank |
| 2014/0224815 A1 | 8/2014 | Gallem |
| 2014/0231456 A1 | 8/2014 | Marshall |
| 2014/0291278 A1 | 10/2014 | Colin |
| 2014/0323975 A1 | 10/2014 | Thornton |
| 2015/0136622 A1 | 5/2015 | Genosar |
| 2015/0165123 A1 | 6/2015 | Thornton |
| 2015/0202372 A1 | 7/2015 | Ali |
| 2015/0283332 A1 | 10/2015 | Woehr |
| 2015/0359708 A1 | 12/2015 | Boomgard |
| 2016/0022541 A1 | 1/2016 | Dalal |
| 2016/0063215 A1 | 3/2016 | Zamer |
| 2016/0074586 A1 | 3/2016 | Mernøe |
| 2016/0120749 A1 | 5/2016 | Hansen |
| 2016/0144130 A1 | 5/2016 | Thornton |

(56) References Cited

U.S. PATENT DOCUMENTS

| | | |
|---|---|---|
| 2016/0151240 A1 | 6/2016 | Brandenburger |
| 2016/0175544 A1 | 6/2016 | Koska |
| 2016/0206417 A1 | 7/2016 | Levine |
| 2016/0246943 A1 | 8/2016 | Lake |
| 2017/0007767 A1 | 1/2017 | Schabbach |
| 2017/0128676 A1 | 5/2017 | Spallek |
| 2018/0072480 A1 | 3/2018 | Genosar |
| 2018/0193565 A1 | 7/2018 | Koska |
| 2018/0193571 A1 | 7/2018 | Koska |
| 2018/0193572 A1 | 7/2018 | Koska |
| 2018/0197143 A1 | 7/2018 | Daub |
| 2018/0235839 A1 | 8/2018 | Johnson |
| 2018/0235840 A1 | 8/2018 | Genosar |
| 2018/0280234 A1 | 10/2018 | Brevik-Andersen |
| 2019/0009068 A1 | 1/2019 | Margoosian |
| 2019/0046402 A1 | 2/2019 | Desbrosses |
| 2019/0060168 A1 | 2/2019 | Koska |
| 2019/0060573 A1 | 2/2019 | Consolaro |
| 2019/0156931 A1 | 5/2019 | Skoda |
| 2019/0214116 A1 | 7/2019 | Eberting |
| 2019/0224424 A1 | 7/2019 | Helmer |
| 2020/0100985 A1 | 4/2020 | Auerbach |
| 2020/0118164 A1 | 4/2020 | Defrank |
| 2020/0129698 A1 | 4/2020 | Chowdhury |
| 2020/0164563 A1 | 5/2020 | Spallek |
| 2020/0172271 A1 | 6/2020 | Colangelo |
| 2020/0246547 A1 | 8/2020 | Glenting |
| 2020/0276082 A1 | 9/2020 | Koska |
| 2020/0384186 A1 | 12/2020 | Consolaro |
| 2021/0030965 A1 | 2/2021 | Koska |
| 2021/0128835 A1 | 5/2021 | Koska |
| 2021/0244888 A1 | 8/2021 | Ryan |
| 2021/0353538 A1 | 11/2021 | Humeniuk |
| 2022/0024616 A1 | 1/2022 | Lema Martinez |
| 2022/0041317 A1 | 2/2022 | Hammer |
| 2022/0133695 A1 | 5/2022 | Terraz Mendoza |
| 2022/0203596 A1 | 6/2022 | Yoshino |
| 2022/0273923 A1 | 9/2022 | Zeira |
| 2022/0273924 A1 | 9/2022 | Kamen |
| 2022/0315296 A1 | 10/2022 | Gamboa Burgos |
| 2022/0323301 A1 | 10/2022 | Koska |
| 2022/0336074 A1 | 10/2022 | Bakos |
| 2022/0336076 A1 | 10/2022 | Albertini |
| 2022/0371873 A1 | 11/2022 | Hayakawa |
| 2022/0401300 A1 | 12/2022 | Ikeda |
| 2022/0409830 A1 | 12/2022 | Shahaf |
| 2023/0045719 A1 | 2/2023 | Koska |
| 2023/0064428 A1 | 3/2023 | Price |
| 2023/0081577 A1 | 3/2023 | Walker et al. |
| 2023/0087192 A1 | 3/2023 | Ferreri |
| 2023/0099753 A1 | 3/2023 | Genosar |
| 2023/0141404 A1 | 5/2023 | Price |
| 2023/0158255 A1 | 5/2023 | Federico |
| 2023/0173178 A1 | 6/2023 | Clapham |
| 2023/0190581 A1 | 6/2023 | Hover |
| 2023/0192346 A1 | 6/2023 | Bouteloup |
| 2023/0192367 A1 | 6/2023 | Luigi |
| 2023/0201387 A1 | 6/2023 | Wendy |
| 2023/0226276 A1 | 7/2023 | Amiri |
| 2023/0226743 A1 | 7/2023 | Schnell |
| 2023/0248897 A1 | 8/2023 | Murray |
| 2023/0248957 A1 | 8/2023 | Juergen |
| 2024/0009397 A1 | 1/2024 | In |
| 2024/0009398 A1 | 1/2024 | Koska |
| 2024/0058217 A1 | 2/2024 | Price |

FOREIGN PATENT DOCUMENTS

| | | |
|---|---|---|
| CA | 2105031 | 3/1994 |
| CN | 1196023 A | 10/1998 |
| CN | 104640594 | 5/2015 |
| CN | 112829265 A | 5/2021 |
| CN | 115259051 A | 11/2022 |
| CN | 217891819 U | 11/2022 |
| CN | 217894251 U | 11/2022 |
| CN | 218020077 U | 12/2022 |
| EP | 0310227 | 4/1989 |
| EP | 0388360 | 9/1990 |
| EP | 0685400 | 12/1995 |
| EP | 0849173 A1 | 6/1998 |
| EP | 0903180 | 3/1999 |
| EP | 0930238 A1 | 7/1999 |
| EP | 1726285 | 11/2006 |
| EP | 2554201 | 2/2013 |
| EP | 2554207 | 2/2013 |
| EP | 2571553 | 3/2013 |
| EP | 2665502 | 11/2013 |
| EP | 2919834 | 9/2015 |
| EP | 3173113 | 5/2017 |
| EP | 3518860 | 8/2019 |
| FR | 2990687 A1 | 11/2013 |
| GB | 2490111 | 10/2012 |
| GB | 2495741 | 4/2013 |
| GB | 2495741 A | 4/2013 |
| IN | 201741030340 | 1/2019 |
| JP | 2009183909 A | 8/2009 |
| JP | 2015109883 | 6/2015 |
| JP | 2019034072 | 3/2019 |
| KR | 200345715 | 3/2004 |
| KR | 100615527 | 8/2006 |
| RU | 2643432 | 2/2018 |
| WO | 1989007462 | 8/1989 |
| WO | 1993017728 | 9/1993 |
| WO | 1997010156 | 3/1997 |
| WO | 1998025660 | 6/1998 |
| WO | 1999043549 | 9/1999 |
| WO | 0018648 A1 | 4/2000 |
| WO | 2001043799 | 6/2001 |
| WO | 2004055143 | 7/2004 |
| WO | 2007007178 A1 | 1/2007 |
| WO | 2008086552 | 7/2008 |
| WO | 2010081174 | 7/2010 |
| WO | 2011008190 | 1/2011 |
| WO | 2011026050 | 3/2011 |
| WO | 2011035503 A1 | 3/2011 |
| WO | 2011075798 | 6/2011 |
| WO | 2012011115 | 1/2012 |
| WO | 2012026551 | 3/2012 |
| WO | 2012064761 | 5/2012 |
| WO | 2012099898 | 7/2012 |
| WO | 2012137945 | 10/2012 |
| WO | 2012148043 | 11/2012 |
| WO | 2012156822 | 11/2012 |
| WO | 2013114357 | 8/2013 |
| WO | 2013149042 A1 | 10/2013 |
| WO | 2014035935 | 3/2014 |
| WO | 2014135108 | 9/2014 |
| WO | 2014135108 A1 | 9/2014 |
| WO | 2014184121 | 11/2014 |
| WO | 2014189761 A1 | 11/2014 |
| WO | 2015036536 | 3/2015 |
| WO | 2015045740 | 4/2015 |
| WO | 2015074087 | 5/2015 |
| WO | 2015134307 | 9/2015 |
| WO | 2015145902 | 10/2015 |
| WO | 2015187518 | 12/2015 |
| WO | 2015200261 A1 | 12/2015 |
| WO | 2016032814 | 3/2016 |
| WO | 2016097872 | 6/2016 |
| WO | 2017001918 | 1/2017 |
| WO | 2017001919 | 1/2017 |
| WO | 2017001921 | 1/2017 |
| WO | 2017001922 | 1/2017 |
| WO | 2017001923 | 1/2017 |
| WO | 2017001925 | 1/2017 |
| WO | 2017103954 A1 | 6/2017 |
| WO | 2017125859 | 7/2017 |
| WO | 2017187262 | 11/2017 |
| WO | 2017187262 A1 | 11/2017 |
| WO | 2018002113 | 1/2018 |
| WO | 2018028820 | 2/2018 |
| WO | 2019040575 A1 | 2/2019 |
| WO | 2019099954 | 5/2019 |
| WO | 2019108577 A1 | 6/2019 |

(56) References Cited

FOREIGN PATENT DOCUMENTS

| | | |
|---|---|---|
| WO | 2019154600 | 8/2019 |
| WO | 2019164478 | 8/2019 |
| WO | 2019246435 | 12/2019 |
| WO | 2021059213 | 4/2021 |
| WO | 2021079404 | 4/2021 |
| WO | 2021186485 | 9/2021 |
| WO | 2021186485 A1 | 9/2021 |
| WO | 2021207040 | 10/2021 |
| WO | 2021226564 | 11/2021 |
| WO | 2022002863 | 1/2022 |
| WO | 2022005310 | 1/2022 |
| WO | 2022026275 | 2/2022 |
| WO | 2022053948 | 3/2022 |
| WO | 2022091003 | 5/2022 |
| WO | 2022112543 | 6/2022 |
| WO | 2022117361 | 6/2022 |
| WO | 2022120269 | 6/2022 |
| WO | 2022133283 | 6/2022 |
| WO | 2022135945 | 6/2022 |
| WO | 2022115598 | 8/2022 |
| WO | 2022180376 | 9/2022 |
| WO | 2022180488 | 9/2022 |
| WO | 2022185350 | 9/2022 |
| WO | 2022186886 | 9/2022 |
| WO | 2022186888 | 9/2022 |
| WO | 2022204408 | 9/2022 |
| WO | 2022207136 | 10/2022 |
| WO | 2022208318 | 10/2022 |
| WO | 2022208488 | 10/2022 |
| WO | 2022256834 | 12/2022 |
| WO | 2022268253 | 12/2022 |
| WO | 2022269651 | 12/2022 |
| WO | 2023281194 | 1/2023 |
| WO | 2023018840 | 2/2023 |
| WO | 23045589 | 3/2023 |
| WO | 23045590 | 3/2023 |
| WO | 23049213 | 3/2023 |
| WO | 2023039126 | 3/2023 |
| WO | 2023045589 A1 | 3/2023 |
| WO | 2023045590 A1 | 3/2023 |
| WO | 2023049213 | 3/2023 |
| WO | 2023086515 A1 | 5/2023 |
| WO | 2023091358 | 5/2023 |
| WO | 2023102008 | 6/2023 |
| WO | 2023104995 | 6/2023 |
| WO | 2023122619 | 6/2023 |
| WO | 2023147491 | 8/2023 |
| WO | 2023244561 | 12/2023 |
| WO | 2024163988 | 8/2024 |

OTHER PUBLICATIONS

Office Action for Chinese Application 201680050853.3 dated Mar. 18, 2020; 3 pps.
Office Action for Chinese Application 201680050853.3 dated Nov. 27, 2020; 3 pps.
Office Action for Chinese Application 201780025582.0 dated Oct. 30, 2020; 2 pps.
Office Action for Chinese Application 201880087016.7 dated Feb. 24, 2022; 7 pps.
Office Action for Chinese Application 201880087016.7 dated Sep. 14, 2021; 3 pps.
Office Action for Indian Application 201827038286 dated Aug. 6, 2021; 6 pps.
Office Action for Indian Application 201827038286 dated Jul. 2, 2021; 8 pps.
Office Action for Korean Patent Application No. 10-2018-7030866 dated Mar. 30, 2022; 4 pps.
Office Action for Korean Patent Application No. 10-2018-7030866 dated Sep. 24, 2021; 17 pps.
Office Action for Mexican Application MX/a/2018/000257 dated Mar. 2, 2022; 5 pps.
Office Action for Mexican Application MX/a/2018/000258 dated Jul. 6, 2022; 3 pps.
Office Action for Mexican Application MX/a/2018/000258 dated Jul. 18, 2022; 5 pps.
Search Report for European Application 18877931.8 dated Jul. 7, 2021; 9 pps.
Search Report for European Application 18877931.8 dated Oct. 19, 2021; 10 pps.
Supplemental European Search Report for European Application No. 19823345.4 dated Feberuary 7, 2022; 6 pps.
Syrette "https://en.wikipedia.org/wiki/Syrette" download date: Apr. 23, 2020; 2 pps.
Woodstock Sterile Solutions https://woodstocksterilesolutions.com/manufacturing-capability/ Date Accessed Mar. 3, 2023 (Year: 2023).
Written Opinion for Application PCT/IB2021/058168 dated Nov. 11, 2021; 9 pps.
Written Opinion for Application PCT/IB2021/059993 dated Nov. 22, 2021; 10 pps.
Written Opinion for Application PCT/US2021/025683 dated Jul. 8, 2021; 4 pps.
Written Opinion for Application PCT/US2022/49608 dated Feb. 16, 2023; 6 pps.
Written Opinion for Application PCT/US21/042671 dated Nov. 5, 2021; 9 pps.
Written Opinion for Application PCT/US21/31452 dated Sep. 1, 2021; 15 pps.
Written Opinion for Application PCT/US21/61991 dated Feb. 16, 2022; 9 pps.
Written Opinion for Application PCT/US22/44291 dated Dec. 22, 2022; 5 pps.
Written Opinion for PCT/IB2016/001026 dated Nov. 7, 2016; 5 pps.
Written Opinion for PCT/IB2016/001027 dated Nov. 2, 2016; 5 pps.
Written Opinion for PCT/IB2016/001033 dated Dec. 7, 2016; 6 pps.
Written Opinion for PCT/IB2016/001050 dated Nov. 14, 2016; 5 pps.
Written Opinion for PCT/IB216/001042 dated Dec. 20, 2016; 6 pps.
Written Opinion for PCT/IIB2016/001034 dated Dec. 9, 2016; 6 pps.
Written Opinion for PCT/US21/064155 dated Mar. 21, 2022; 3 pps.
Written Opinion for PCT/US22/40006 dated Nov. 7, 2022; 6 pps.
Written Opinion for WO 2016097872 dated May 9, 2016; 2 pps.
Written Opinion for WO2017/187262 dated Sep. 4, 2017; 7 pps.
Written Opinion or PCT/US18/61696 dated Mar. 7, 2019; 3 pps.
Written Opinion or PCT/US2019/038302 dated Dec. 19, 2019; 4pps.
Allowance Notification for Chinese Application 201680050853.3 dated Jun. 8, 2021; 1 pp.
Allowance Notification for Chinese Application 201780025582.0 dated Jun. 21, 2021; 1 pp.
Bufus Plastic Drop https://www.alamy.com/stock-photo-bufus-plastic-drop-ampoule-vial-spray-the-medicine-cast-resin-sealed 131358830.html Nov. 10, 2015 (Year: 2015).
Communication prusuant to Article 94(3) EPC for EP 17730256.9 dated Aug. 31, 2022; 5 pps.
Examination Report for PCT/IB2015/002531 dated May 28, 2020; 5 pps.
International Preliminary Report on Patentability for PCT/US18/61696 dated May 28, 2020; 4pps.
International Search Report for Application PCT/IB2016/001033 dated Dec. 9, 2016; 4 pps.
International Search Report for Application PCT/IB2016/001034 dated Dec. 13, 2016; 3 pps.
International Search Report for Application PCT/IB2016/001042 dated Dec. 22, 2016; 3 pps.
International Search Report for Application PCT/IB2021/058168 dated Nov. 11, 2021; 6 pps.
International Search Report for Application PCT/IB2021/058168 dated Nov. 22, 2021; 6 pps.
International Search Report for Application PCT/IB2021/059993 dated Nov. 22, 2021; 8 pps.
International Search Report for Application PCT/US2021/025683 dated Jul. 8, 2021; 2 pps.

(56) References Cited

OTHER PUBLICATIONS

International Search Report for Application PCT/US2022/49608 dated Feb. 21, 2023; 3 pps.
International Search Report for Application PCT/US21/042671 dated Nov. 5, 2021; 2 pps.
International Search Report for Application PCT/US21/064155 dated Mar. 21, 2022; 2 pps.
International Search Report for Application PCT/US21/31452 dated Sep. 1, 2021; 2 pps.
International Search Report for Application PCT/US21/61991 dated Feb. 16, 2022; 2 pps.
International Search Report for Application PCT/US22/40006 dated Nov. 7, 2022; 5 pps.
International Search Report for Application PCT/US22/44291 dated Dec. 22, 2022; 5 pps.
International Search Report for PCT/IB2016/001027 dated Jan. 5, 2017; 2 pps.
International Search Report for PCT/IB2016/001050 dated Nov. 15, 2016; 2 Pps.
International Search Report for PCT/US18/61696 dated Mar. 7, 2019; 2 pps.
International Search Report for PCT/US2019/038302 dated Dec. 19, 2019; 2 pps.
International Search Report for WO 2016097872 dated May 9, 2016, 1 pps.
International Search Report for WO2017/187262 dated Sep. 4, 2017; 3 pps.
International Search Report or PCT/IB2016/001026 dated Nov. 8, 2016; 3 pps.
Notice of Acceptance for Australian Application 2017256152 dated Apr. 11, 2022; 3 pps.
Notice of Allowance dated Mar. 21, 2023 for U.S. Appl. No. 29/803,121 (pp. 1-9).
Notice of Allowance dated May 5, 2023 for U.S. Appl. No. 29/803,121 (pp. 1-2).
Notice of Grant for 16774977.9 dated Mar. 12, 2020; 2 pps.
Office Action (Final Rejection) dated Dec. 28, 2022 for U.S. Appl. No. 16/876,417 (pp. 1-6).
Office Action (Final) for U.S. Appl. No. 14/575,635 dated Dec. 14, 2017; 44 pps.
Office Action (Non-Final Rejection) dated Jan. 12, 2022 for U.S. Appl. No. 16/169,983 (pp. 1-12).
Office Action (Non-Final Rejection) dated Jun. 8, 2022 for U.S. Appl. No. 16/876,417 (pp. 1-9).
Office Action (Non-final) for U.S. Appl. No. 14/575,635 dated Mar. 23, 2017; 44 pps.
Office Action (Non-final) for U.S. Appl. No. 14/575,635 dated Oct. 9, 2018; 39 pps.
Office Action (Non-final) for U.S. Appl. No. 15/741,009 dated Oct. 2, 2019; 6 pps.
Office Action (Non-final) for U.S. Appl. No. 15/741,011 dated Oct. 2, 2019; 8 pps.
Office Action (Notice of Allowance and Fees Due (PTOL-85)) dated Feb. 2, 2023 for U.S. Appl. No. 16/876,417; pp. 1-5).
Office Action (Notice of Allowance and Fees Due (PTOL-85)) dated Feb. 23, 2022 for U.S. Appl. No. 16/169,983 (pp. 1-7).
Office Action (Notice of Allowance and Fees Due (PTOL-85)) dated May 17, 2022 for U.S. Appl. No. 16/169,983 (pp. 1-7).
Office Action (Notice of Allowance and Fees Due (PTOL-85)) dated Jun. 2, 2022 for U.S. Appl. No. 16/169,983 (pp. 1-3).
Office Action (Notice of Allowance and Fees Due (PTOL-85)) dated Jul. 10, 2020 for U.S. Appl. No. 15/741,012 (pp. 1-6).
Office Action (Notice of Allowance and Fees Due (PTOL-85)) dated May 17, 2022 for U.S. Appl. No. 16/169,983; 7 pps.
Office Action for U.S. Appl. No. 15/741,009 dated Oct. 2, 2019; 6 pps.
Office Action for U.S. Appl. No. 15/741,011 dated Oct. 2, 2019; 8pps.
Office Action for U.S. Appl. No. 15/741,012 dated Oct. 2, 2019; 7pps.
Office Action for U.S. Appl. No. 16/876,417 dated Jun. 8, 2022; 9 pps.
Office Action for Australian Application 2017256152 dated Jul. 29, 2021; 6 pps.
Australian Application 2022203652 dated Oct. 20, 2023; 7 pps.
Final Office Action dated Dec. 21, 2023 for U.S. Appl. No. 17/849,780; 13 pgs.
Final Office Action for U.S. Appl. No. 15/741,012 dated Oct. 2, 2019; 7 pps.
Final Office Action for U.S. Appl. No. 14/575,635 dated Dec. 14, 2017; 16 pps.
Final Office Action for U.S. Appl. No. 16/876,417 dated Dec. 28, 2022; 6 pps.
International Search Report for PCT Application No. PCT/US21/064155 dated Mar. 21, 2022; 2 pps.
International Search Report for PCT/IB2015/002531 dated Jan. 5, 2017; 3 pps.
International Search Report for PCT/IB2016/001026 dated Jan. 5, 2017; 4 pps.
International Search Report for PCT/IB2016/001027 dated Jan. 5, 2017; 3 pps.
International Search Report for PCT/US23/25123 dated Sep. 29, 2023; 2 pps.
International Written Opinion for PCT Application No. PCT/US21/064155 dated Mar. 21, 2022; 3 pps.
Notice of Allowance for U.S. Appl. No. 17/072,498 dated Jun. 30, 2023; 7 pgs.
Notice of Allowance dated Jun. 30, 2023 for U.S. Appl. No. 17/072,498 (pp. 1-7).
Notice of Allowance for U.S. Appl. No. 15/741,012 dated Jul. 10, 2020; 7 pps.
Notice of Allowance for U.S. Appl. No. 16/876,417 dated Feb. 2, 2023; 5 pps.
Notice of Hearing for Indian Application 201827038286 dated Jan. 17, 2024; 2 pps.
Office Action (Final Rejection) dated Dec. 21, 2023 for U.S. Appl. No. 17/849,780 (pp. 1-13).
Office Action (Non-Final Rejection) dated Feb. 7, 2023 for U.S. Appl. No. 17/072,498 (pp. 1-9).
Office Action (Non-Final Rejection) dated Aug. 8, 2023 for U.S. Appl. No. 17/849,780; pp. 1-15).
Office Action (Notice of Allowance and Fees Due (PTOL-85)) dated Jun. 30, 2023 for U.S. Appl. No. 17/072,498 (pp. 1-7).
Office Action for Australian Application 2022203652 dated Jun. 23, 2023; 5 pps.
Office Action for Australian Application 2022203652 dated Oct. 20, 2023; 7 pps.
Office Action for Canadian Application 3021989 dated May 18, 2023; 3 pps.
Office Action for Chinese Application 201880087016.7 dated Jun. 15, 2022; 10 pps.
Office Action for European Patent Application 18877931.8 dated May 23, 2023; 4 pps.
Office Action for Indian Patent Application 201827038286 dated Jun. 8, 2021; 6 pps.
Office Action for Indian Patent Application 202027021653 dated May 6, 2022; 5 pps.
Office Action for Korean Patent Application 10-2018-7003178 dated Feb. 20, 2023; 2 pps.
Office Action for Korean Patent Application 10-2020-7017317 dated Aug. 1, 2023; 2 pps.
Office Action for Mexican Patent Application MX/a/2017/008000 dated Apr. 26, 2022; 6 pps.
Office Action for Mexican Patent Application MX/a/2018/000257 dated Mar. 2, 2022; 4 pps.
Office Action for Mexican Patent Application MX/a/2018/012967 dated Nov. 1, 2022; 3 pps.
Office Action for U.S. Appl. No. 14/575,635 dated Mar. 3, 2017; 25 pps.
Office Action for U.S. Appl. No. 14/575,635 dated Oct. 9, 2018; 16 pps.
Office Action for U.S. Appl. No. 15/741,011 dated Oct. 2, 2019; 7 pps.

(56) References Cited

OTHER PUBLICATIONS

Office Action for U.S. Appl. No. 17/072,498 dated Feb. 7, 2023; 9 pps.
Written Opinion for PCT/US23/25123 dated Sep. 29, 2023; 9 pps.
Written Opinion for PCT/IB2015/002531 dated Jun. 23, 2016; 6 pps.
Written Opinion for PCT/IB2016/001026 dated Jan. 5, 2017; 5 pps.
Written Opinion for PCT/IB2016/001027 dated Jan. 5, 2017; 5 pps.
Extended European Search Report (EESR) for European Patent Application No. 21907935.7 mailed on Sep. 23, 2024 (7 pages).
International Search Report for PCT/US24/14394 dated Jul. 29, 2024; 6 pps.
Notice of Allowance dated Jul. 17, 2024 for U.S. Appl. No. 29/736,603; 8 pgs.
Notice of Allowance/Intention to Grant for Canadian Patent Application No. 3,021,989 mailed on Oct. 15, 2024 (1 page).
Office Action (Non-Final Rejection; dated Apr. 23, 2024 for U.S. Appl. No. 17/129,593 (pp. 1-20).
Office Action (Notice of Allowance and Fees Due (PTOL-85)) dated Apr. 24, 2024 for U.S. Appl. No. 17/849,780; 7 pgs.
Office Action (Notice of Allowance and Fees Due (PTOL-85)) dated May 23, 2024 for U.S. Appl. No. 17/849,780; 3 pgs.
Office Action (Notice of Allowance and Fees Due (PTOL-85)) dated Jul. 15, 2024 for U.S. Appl. No. 17/849,780, 3 pgs.
Refresh Classic Lubricant Eye Drops, first available May 21, 2007, amazon.com, [online], [site visited Jul. 8, 2024], Available from internet URL: https://www.amazon.com/dp/B000R2VCIA (Year: 2007).
Written Opinion for PCT/US24/14394 dated Jul. 29, 2024; 10 pps.

SYSTEMS AND METHODS FOR FLUID DELIVERY MANIFOLDS

CROSS-REFERENCE TO RELATED APPLICATIONS

This application claims benefit and priority to, and is a Continuation of U.S. patent application Ser. No. 16/876,417 filed on May 18, 2020 and titled "SYSTEMS AND METHODS FOR FLUID DELIVERY MANIFOLDS", which issued as U.S. Pat. No. 11,607,369 on Mar. 21, 2023 and which itself claims benefit and priority to and is a Continuation of International Patent Application No. PCT/US18/61696 titled "SYSTEMS AND METHODS FOR FLUID DELIVERY MANIFOLDS" and filed on Nov. 16, 2018 which itself claims priority to and is a non-provisional of: (i) U.S. Provisional Application Ser. No. 62/587,879 titled "DELIVERY SYSTEM" and filed on Nov. 17, 2017, (ii) U.S. Provisional Application Ser. No. 62/674,565 titled "NFC-Enabled Drug Containing System and Associated Information Layer" and filed on May 21, 2018, and (iii) U.S. Provisional Application Ser. No. 62/680,116 titled "NFC-ENABLED DRUG CONTAINING SYSTEM AND ASSOCIATED INFORMATION LAYER" and filed on Jun. 4, 2018; the contents of each of which are hereby incorporated by reference herein in their entirety.

BACKGROUND

Every year, millions of people become infected and die from a variety of diseases, some of which are vaccine-preventable. Although vaccination has led to a dramatic decline in the number of cases of several infectious diseases, some of these diseases remain quite common. In many instances, large populations of the world, particularly in developing countries, suffer from the spread of vaccine-preventable diseases due to ineffective immunization programs, either because of poor implementation, lack of affordable vaccines, or inadequate devices for administering vaccines, or combinations thereof.

Some implementations of immunization programs generally include administration of vaccines via a typical reusable syringe. However, in many situations, particularly in developing countries, the administration of vaccines occur outside of a hospital and may be provided by a non-professional, such that injections are given to patients without carefully controlling access to syringes. The use of reusable syringes under those circumstances increases the risk of infection and spread of blood-borne diseases, particularly when syringes, which have been previously used and are no longer sterile, are used to administer subsequent injections. For example, the World Health Organization (WHO) estimates that blood-borne diseases, such as Hepatitis and human immunodeficiency virus (HIV), are being transmitted due to reuse of such syringes, resulting the death of more than one million people each year.

Previous attempts at providing single-use or disposable injection devices to remedy such problems in the industry have achieved measurable success but have failed to adequately remedy the existing problems. Pre-filled, single-use injection devices manufactured via injection molding or Form-Fill-Seal (FFS) processes, such as the Uniject™ device available from the Becton, Dickinson and Company of Franklin Lakes, NJ, for example, while offering precise manufacturing tolerances in the range of two thousandths of an inch (0.002-in; 50.8 μm) to four thousandths of an inch (0.004-in; 101.6 μm)—for hole diameters in molded parts, require separate sterilization processes (e.g., gamma radiation) that are not compatible with certain fluids, provide production rates limited to approximately nine thousand (9,000) non-sterile units per hour, and can be provided to an end-user for approximately one dollar and forty cents ($1.40) per dose/unit.

BRIEF DESCRIPTION OF THE DRAWINGS

An understanding of embodiments described herein and many of the attendant advantages thereof may be readily obtained by reference to the following detailed description when considered with the accompanying drawings, wherein.

DETAILED DESCRIPTION

I. Introduction

Embodiments of the present invention provide systems and methods for fluid delivery manifolds that overcome the drawbacks of current delivery devices and methods. For example, the delivery system of some embodiments may include a Blow-Fill-Seal (BFS) package coupled to a fluid delivery manifold and/or a safety cap manifold. In some embodiments, an administration member such as a needle may be selectively actuated by application of force to the fluid delivery manifold and/or a safety cap manifold, causing the administration member to pierce a fluid reservoir of at least one BFS vial of the BFS package. Utilization of such systems that employ BFS vials and/or a fluid delivery manifold may be advantageous and may address various shortcomings of pervious systems.

BFS vials may, for example, offer a less expensive alternative to vials or devices created via other manufacturing techniques. In some embodiments, BFS vials (e.g., due to the nature of the BFS manufacturing process) may not require separate sterilization (e.g., an may accordingly be compatible with a wider array of fluids), may provide enhanced production rates of approximately thirty thousand (30,000) sterile/aseptic units per hour, and/or may be provided to an end-user for approximately forty-five cents ($0.45) per dose/unit. In some embodiments, these advantages may come with an attendant drawback of reduced manufacturing tolerances. BFS processes may, for example, offer less precise manufacturing tolerances in the range of five hundredths of an inch (0.05-in; 1.27 mm) to fifteen hundredths of an inch (0.15-in; 3.81 mm)—for linear dimensions, e.g., in accordance with the standard ISO 2768-1 "General tolerances for linear and angular dimensions without individual tolerance indications" published by the International Organization for Standardization (ISO) of Geneva, Switzerland (Nov. 15, 1989).

According to some embodiments, a single-dose, disposable, and/or non-refillable fluid delivery device may be provided despite the presence of the less precise manufacturing tolerances of the BFS vials, by utilization of the systems and methods described herein.

II. Fluid Delivery Manifold Systems

Figure 1:
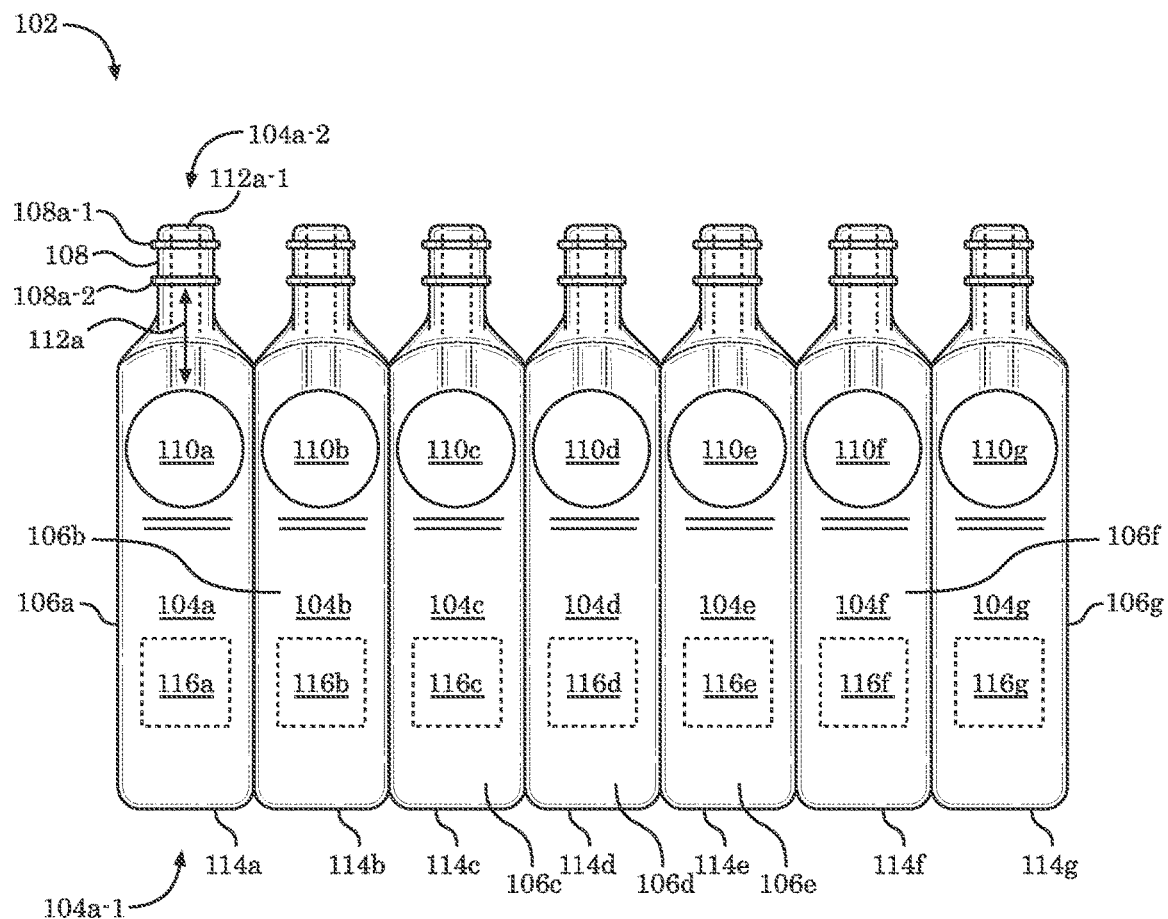
FIG. 1 is a front view of BFS vial package according to some embodiments.

Referring initially to FIG. 1, for example, a front view of BFS vial package 102 according to some embodiments is shown. The BFS vial package 102 may, for example, comprise and/or define a plurality of individual-dose BFS vials 104a-g joined, coupled, and/or formed together, e.g., as depicted. In some embodiments, and as illustrated with respect to a first one of the plurality of BFS vial 104a, the first BFS vial 104a may comprise and/or define a first or proximate end 104a-1 and a second or distal end 104a-2. Disposed therebetween, according to some embodiments, may be a first BFS vial body 106a. In some embodiments, each BFS vial 104a-g may be coupled (e.g., during and/or as a by-product of a BFS formation process) to any adjacent BFS vial 104a-g via the respectively-adjacent BFS bodies 106a-g. The connected series of seven (7) BFS vials 104a-g depicted in FIG. 1 may, for example, be formed together via a single, seven-compartment BFS mold or die (not shown) during a BFS formation process. In some embodiments, fewer or more BFS vials 104a-g may comprise and/or define the BFS vial package 102, as is or becomes known or practicable.

According to some embodiments, each BFS vial 104a-g may comprise and/or define various features such as features molded, formed, cut, glued, and/or otherwise coupled thereto. As depicted in FIG. 1 for example, the first BFS vial 104a may comprise a first vial neck 108a (e.g., at or near the distal end 104a-2) upon which various mating features are formed (or otherwise coupled). In some embodiments, the first vial neck 108a may comprise a first or distal exterior radial flange 108a-1 and/or a second or proximate exterior radial flange 108a-2. According to some embodiments, either of the radial flanges 108a-1, 108a-2 and/or a separate mating feature (not shown) on or of the first vial neck 108a may comprise a tab or other radial protrusion that permits indexed mating of the first vial neck 108a with various other components (not shown in FIG. 1). In some embodiments, each of the BFS vials 104a-g may comprise and/or define a fluid reservoir 110a-g, e.g., disposed and/or formed on each respective vial body 106a-g thereof. According to some embodiments, each fluid reservoir 110a-g may store, house, and/or accept a single dose of fluid such as one or more medications, vaccines, solutions, and/or other therapeutic, restorative, preventative and/or curative agents. In some embodiments, a nitrogen bubble (not shown) may be disposed in the fluid reservoirs 110a-g to facilitate expelling of all of the fluid in the case that the fluid reservoirs 110a-g are squeezed and/or compressed by a user (not shown).

Radially inward compressive force applied to a first fluid reservoir 110a of the first BFS vial 104a may, for example, cause the first fluid reservoir 110a to collapse radially inward, forcing the fluid stored therein into a fluid channel 112a disposed in the first vial neck 108a. The first vial neck 108a may comprise a tube or passage, for example, that but for a fluid seal 112a-1 disposed at the distal end 104a-2, would form an opening at the distal end 104a-2 through which the fluid may flow when expelled from the first fluid reservoir 110a. In some embodiments, the first vial body 106a may comprise and/or define a flat or grip portion 114a disposed between the first fluid reservoir 110a and the proximate end 104a-1 of the first BFS vial 104a. The grip portion 114a may, for example, comprise a flat element that permits axial force to be applied to the first BFS vial 104a without causing such axial force to be applied to the first fluid reservoir 110a (e.g., for engaging an administering element (not shown) as described herein).

In some embodiments, the BFS vial package 102 may comprise an indicia imprinting thereon (and/or therein) and/or upon each individual BFS vial 104a-g (e.g., on the grip portion 114a of the first BFS vial 104a). Exemplary indicia may include, but is not limited to, lot number, expiration date, medication information (e.g., type, quantity, etc.), a security stamp (color changing temperature sensor to provide indication of whether BFS vials 104a-g have or have not been maintained at required temperature), as well as a dosage and/or measurement line provided on each BF vial 104a-g. While seven (7) BFS vials 104a-g are depicted in FIG. 1 as being coupled to and/or comprising the BFS vial package 102, fewer or more BFS vials 104a-g may be coupled to the BFS vial package 102 as is or becomes desirable and/or practicable.

According to some embodiments, the BFS vial package 102 and/or one or more of the BFS vials 104a-g may comprise and/or be coupled to one or more electronic devices 116a-g. The electronic devices 116a-g may comprise, for example, one or more passive inductive, Radio Frequency IDentification (RFID), Near-Field-Communication (NFC), processing, power storage, and/or memory storage devices. In some embodiments, the electronic devices 116a-g may store, process, receive, and/or transmit various data elements such as to track geographical movement of the BFS vial package 102 and/or to verify or confirm that a particular BFS vial 104a-g should be utilized for administration to a particular recipient.

In some embodiments for example, in the case that a user (whether a healthcare worker, a patient who is self-injecting or a friend or family member injecting a patient) is about to inject a fluid agent utilizing the first BFS vial 104a that comprises a first electronic device 116a such as an NFC chip, the user may first open an appropriate app on his/her mobile device (not shown) and tap (or bring into proximity) the first BFS vial 104a and/or the first electronic device 116a to the mobile device to initiate communications therebetween. This may allow, in some embodiments, the app to verify the injection by verifying and/or authenticating one or more of the following: (i) that the fluid is the correct fluid agent the patient is supposed to be receiving (e.g., based on a comparison of fluid data stored by the first electronic device 116a and patient information stored in a separate memory device, e.g., of the user's mobile device); (ii) that the injection is being administered within an appropriate window of time (e.g., by comparing a current time and/or date to a time and/or date stored and/or referenced by data of the first electronic device 116a); (iii) that the first BFS vial 104a and/or fluid therein has not been compromised and/or is not expired. According to some embodiments, any of the foregoing may be verified based on records of the patient stored in the app on the mobile device and/or accessible to the app via the internet or a cloud-based system and/or data stored in the first electronic device 116a. In some embodiments, in the case that the required (or desired) verifications are processed successfully, the user may be authorized to perform the injection (e.g., an approval indicator may be output to the user via a screen of the app). The user may be motivated to only inject upon receiving the approval via the app because the user may only receive rewards via the app if he/she performs approved injections. In some embodiments, the user may also be requested to upload a photo of the first BFS vial 104a and/or the injection site (not shown) after the injection (e.g., to finalize qualification for a reward and/or to qualify for an additional reward). According to some embodiments, a reward may be provided to the user via the user's mobile device, e.g., in response to receiving data descriptive of the administration of the fluid and/or the use of the first BFS vial 104a.

In some embodiments, fewer or more components 104a-g, 104a-1, 104a-2, 106a-g, 108a, 108a-1, 108a-2, 110a-g, 112a, 112a-1, 114a-g, 116a-g and/or various configurations of the depicted components 104a-g, 104a-1, 104a-2, 106a-g, 108a, 108a-1, 108a-2, 110a-g, 112a, 112a-1, 114a-g, 116a-g may be included in the BFS vial package 102 without deviating from the scope of embodiments described herein. In some embodiments, the components 104a-g, 104a-1, 104a-2, 106a-g, 108a, 108a-1, 108a-2, 110a-g, 112a, 112a-1, 114a-g, 116a-g may be similar in configuration and/or functionality to similarly named and/or numbered components as described herein. In some embodiments, the BFS vial package 102 (and/or portion and/or component 104a-g, 104a-1, 104a-2, 106a-g, 108a, 108a-1, 108a-2, 110a-g, 112a, 112a-1, 114a-g, 116a-g thereof) may be utilized in accordance with the method 900 of FIG. 9 herein, and/or portions thereof.

Figure 2:
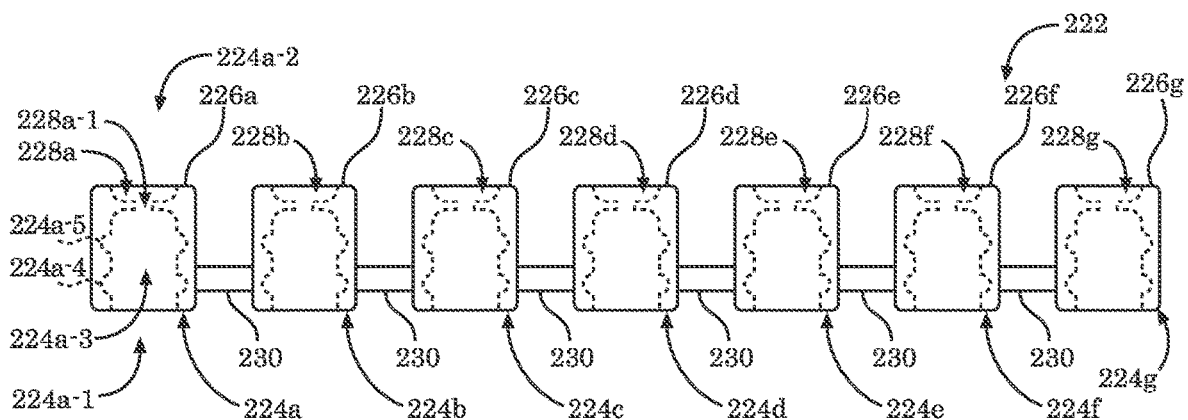
FIG. 2 is a front view of a fluid delivery manifold according to some embodiments.

Turning now to FIG. 2, a front view of a fluid delivery manifold 222 according to some embodiments is shown. The fluid delivery manifold 222 may, for example, be configured to mate with a BFS vial package (not shown; such as the BFS vial package 102 of FIG. 1 herein). In some embodiments, the fluid delivery manifold 222 may comprise a plurality of fluid delivery hubs 224a-g, each, e.g., configured to mate with a BFS vial (not shown; such as the BFS vials 104a-g of FIG. 1 herein). According to some embodiments, one or more of the fluid delivery hubs 224a-g, such as a first one of the fluid delivery hubs 224a, may comprise and/or define a first or proximate end 224a-1 and a second or distal end 224a-2. In some embodiments, the first fluid delivery hub 224a may comprise and/or define a first interior volume 224a-3 comprising one or more internal features such as a first or proximate radial channel 224a-4 and/or a second or distal radial channel 224a-5. According to some embodiments, the fluid delivery hubs 224a-g may comprise hub bodies 226a-g, e.g., a first hub body 226a of the first fluid delivery hub 224a being disposed between the first and second ends 224a-1, 224a-2 thereof. In some embodiments, the hub bodies 226a-g may be substantially cylindrical.

According to some embodiments, the hub bodies 226a-g may comprise and/or define seats 228a-g. As depicted in FIG. 2, for example, the first hub body 226a may comprise a first seat 228a disposed or formed on an upper surface at the distal end 224a-2 of the first hub body 226a. In some embodiments, the first seat 228a may be in communication with the first interior volume 224a-3 via a bore 228a-1 disposed therebetween. The bore 228a-1 may, for example, allow for passage of an administration member (not shown) coupled to provide fluid (e.g., toward the distal end 224a-2) from a BFS vial (not shown in FIG. 2) coupled and/or disposed in the first interior volume 224a-3. According to some embodiments, the seats 228a-g may be sized and/or configured to accept, couple to, and/or mater with a seal, washer, stopper, and/or other element (not shown) disposed therein.

In some embodiments, the hub bodies 226a-g may be joined together to adjacent hub bodies 226a-g via one or more hub connectors 230. The hub connectors 230 and the hub bodies 226a-g may be formed together as a result of a BFS manufacturing process, for example, such as by being extruded from the same plastic and/or polymer material acted upon by a single BFS mold or die. According to some embodiments, the hub connectors 230 may be configured to be easily removed from the hub bodies 226a-g such as by incorporating perforations, stress points, and/or break points that are designed to shear, tear, or sever in response to certain applied forces. The first fluid delivery hub 224a may be separated from an adjacent second fluid delivery hub 224b, for example, in response to a rotational or twisting force being applied to the joint or juncture where a hub connector 230 is coupled to the first hub body 226a (and/or a second hub body 226b). In some embodiments, a designed stress or break point may be disposed at the juncture with the hub bodies 226a-g, in the middle of a length of the hub connectors 230, or as is or becomes desirable and/or practicable. In such a manner, for example, the fluid delivery manifold 222 may be quickly and easily manufactured as a single part while allowing the individual fluid delivery hubs 224a-g to be selectively removed with minimal effort, as is known in the plastic manufacturing arts.

According to some embodiments, fewer or more components 224a-g, 224a-1, 224a-2, 224a-3, 224a-4, 224a-5, 226a-g, 228a-g, 228a-1, 230 and/or various configurations of the depicted components 224a-g, 224a-1, 224a-2, 224a-3, 224a-4, 224a-5, 226a-g, 228a-g, 228a-1, 230 may be included in the fluid delivery manifold 222 without deviating from the scope of embodiments described herein. In some embodiments, the components 224a-g, 224a-1, 224a-2, 224a-3, 224a-4, 224a-5, 226a-g, 228a-g, 228a-1, 230 may be similar in configuration and/or functionality to similarly named and/or numbered components as described herein. In some embodiments, the fluid delivery manifold 222 (and/or portion and/or component 224a-g, 224a-1, 224a-2, 224a-3, 224a-4, 224a-5, 226a-g, 228a-g, 228a-1, 230 thereof) may be utilized in accordance with the method 900 of FIG. 9 herein, and/or portions thereof.

Figure 3:
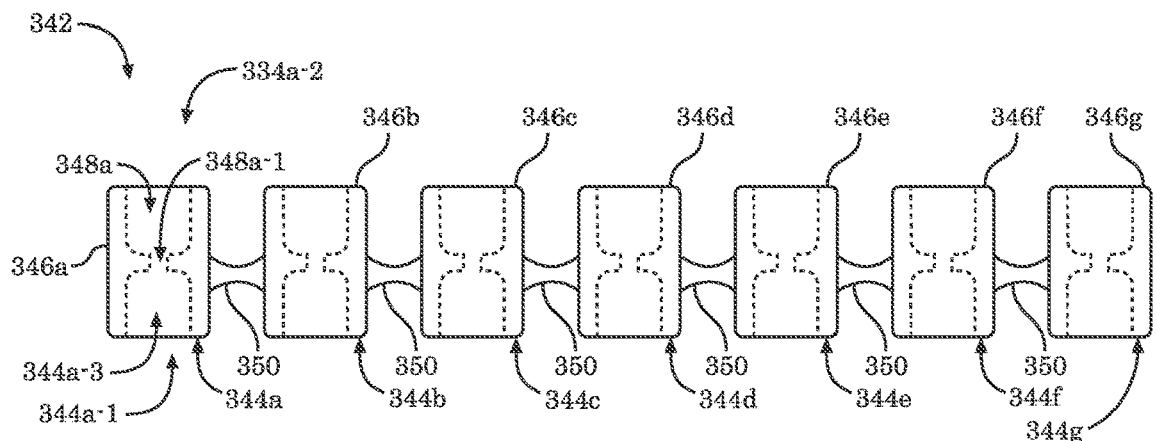
FIG. 3 is a front view of a safety cap manifold according to some embodiments.

Turning now to FIG. 3, a front view of a safety cap manifold 342 according to some embodiments is shown. In some embodiments, the safety cap manifold 342 may be configured to mate with a fluid delivery manifold (not shown) such as the fluid delivery manifold 222 of FIG. 2 herein. The safety cap manifold 342 may, for example, comprise a plurality of safety caps 344a-g each being configured to mate with a respective fluid delivery hub (not shown) such as the fluid delivery hubs 224a-g of FIG. 2 herein. In some embodiments, one or more of the safety caps 344a-g, such as a first one of the safety caps 344a, may comprise and/or define a first or proximate end 344a-1 and a second or distal end 344a-2. In some embodiments, the first safety cap 344a may comprise and/or define a first lower void 344a-3. According to some embodiments, the safety caps 344a-g may comprise safety cap bodies 346a-g, e.g., a first safety cap body 346a of the first safety cap 344a being disposed between the first and second ends 344a-1, 344a-2 thereof. In some embodiments, the safety cap bodies 346a-g may be substantially cylindrical.

According to some embodiments, the safety cap bodies 346a-g may comprise and/or define upper voids 348a-g. As depicted in FIG. 3, for example, the first safety cap body 346a may comprise a first upper void 348a disposed, formed, and/or open at (or closed at) the distal end 344a-2 of the first safety cap body 346a. In some embodiments, the first upper void 348a may be in communication with the first lower void 344a-3 via a passage 348a-1 disposed therebetween. The passage 348a-1 may, for example, allow for passage of an administration member (not shown) housed and/or retained by a fluid delivery hub (not shown) disposed and/or coupled within the first lower void 344a-3.

In some embodiments, the safety cap bodies 346a-g may be joined together to adjacent safety cap bodies 346a-g via one or more cap connectors 350. The cap connectors 350 and the safety cap bodies 346a-g may be formed together as a result of a BFS (or other) manufacturing process, for example, such as by being extruded and/or injected from the same plastic and/or polymer material acted upon by a single BFS (or other) mold or die. According to some embodiments, the cap connectors 350 may be configured to be easily removed from the safety cap bodies 346a-g such as by incorporating perforations, stress points, and/or break points that are designed to shear, tear, or sever in response to certain applied forces. The first safety cap 344a may be separated from an adjacent second safety cap 344b, for example, in response to a rotational or twisting force being applied to the joint or juncture where a cap connector 350 is coupled to the first safety cap body 346a (and/or a second safety cap body 346b). In some embodiments, a designed stress or break point may be disposed at the juncture with the safety cap bodies 346a-g, in the middle of a length of the cap connectors 350, or as is or becomes desirable and/or practicable. In such a manner, for example, the safety cap manifold 342 may be quickly and easily manufactured as a single part while allowing the individual safety caps 344a-g to be selectively removed with minimal effort, as is known in the plastic manufacturing arts.

According to some embodiments, fewer or more components 344a-g, 344a-1, 344a-2, 344a-3, 346a-g, 348a-g, 348a-1, 350 and/or various configurations of the depicted components 344a-g, 344a-1, 344a-2, 344a-3, 346a-g, 348a-g, 348a-1, 350 may be included in the safety cap manifold 342 without deviating from the scope of embodiments described herein. In some embodiments, the components 344a-g, 344a-1, 344a-2, 344a-3, 346a-g, 348a-g, 348a-1, 350 may be similar in configuration and/or functionality to similarly named and/or numbered components as described herein. In some embodiments, the safety cap manifold 342 (and/or portion and/or component 344a-g, 344a-1, 344a-2, 344a-3, 346a-g, 348a-g, 348a-1, 350 thereof) may be utilized in accordance with the methods 900 of FIG. 9 herein, and/or portions thereof.

Figure 4:
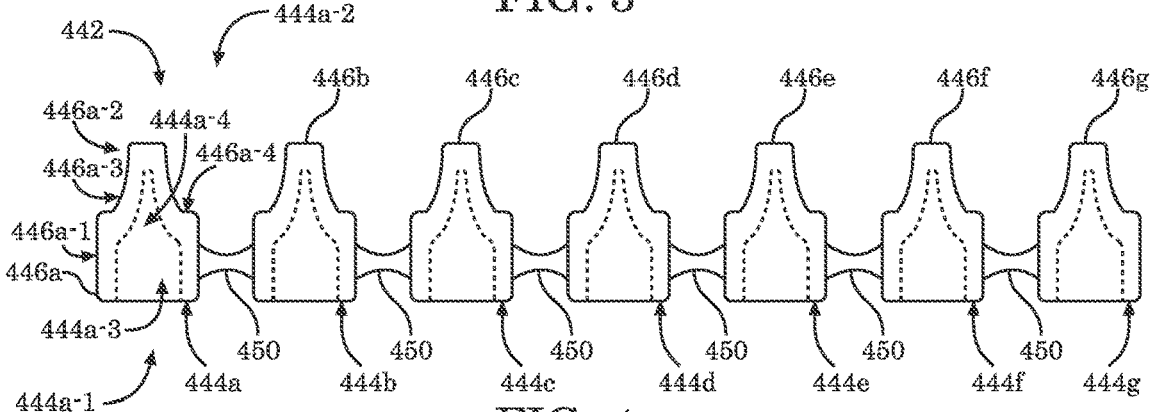
FIG. 4 is a front view of a safety cap manifold according to some embodiments.

Referring now to FIG. 4, a front view of a safety cap manifold 442 according to some embodiments is shown. In some embodiments, the safety cap manifold 442 may be configured to mate with a fluid delivery manifold (not shown) such as the fluid delivery manifold 222 of FIG. 2 herein. The safety cap manifold 442 may, for example, comprise a plurality of safety caps 444a-g each being configured to mate with a respective fluid delivery hub (not shown) such as the fluid delivery hubs 224a-g of FIG. 2 herein. In some embodiments, one or more of the safety caps 444a-g, such as a first one of the safety caps 444a, may comprise and/or define a first or proximate end 444a-1 and a second or distal end 444a-2. In some embodiments, the first safety cap 444a may comprise and/or define a first lower void 444a-3 (e.g., having a first diameter) and/or a first upper void 444a-4 (e.g., having a second diameter) in communication therewith. According to some embodiments, the safety caps 444a-g may comprise safety cap bodies 446a-g, e.g., a first safety cap body 446a of the first safety cap 444a being disposed between the first and second ends 444a-1, 444a-2 thereof. In some embodiments, the safety cap bodies 446a-g may be conically shaped and/or may comprise a plurality of shaped portions.

As depicted in FIG. 4 for example, the first safety cap body 446a may comprise a lower body portion 446a-1 that is cylindrically-shaped with a first outside diameter and an upper body portion 446a-2 that is cylindrically-shaped with a second outside diameter that is smaller that the first outside diameter. According to some embodiments, a smooth transition of the outside surface of the first safety cap body 446a between the first and second outside diameters may define a tapered body portion 446a-3 between the lower body portion 446a-1 and the upper body portion 446a-1. In some embodiments, the upper body portion 446a-2 may be frustoconically-shaped and/or may define therein the upper void 444a-4. The upper void 444a-4 and/or the upper body portion 446a-2 may, for example, allow for passage of an administration member (not shown) housed and/or retained by a fluid delivery hub (not shown) disposed and/or coupled within the first lower void 444a-3.

According to some embodiments, the first safety cap body 446a may comprise and/or define an exterior flange 446a-4. The exterior flange 446a-4 may, for example, be formed and/or defined by the intersection of the upper body portion 446a-2 and the lower body portion 446a-1 (and/or the tapered body portion 446a-3), e.g., having a radial depth based on the difference between the first and second outside diameters thereof. In some embodiments, the exterior flange 446a-4 and/or the tapered body portion 446a-3 may be utilized to apply axial forces on the first safety cap 444a, e.g., to effectuate activation of a fluid delivery system (not shown) as described herein.

In some embodiments, the safety cap bodies 446a-g may be joined together to adjacent safety cap bodies 446a-g via one or more cap connectors 450. The cap connectors 450 and the safety cap bodies 446a-g may be formed together as a result of a BFS (or other) manufacturing process, for example, such as by being extruded and/or injected from the same plastic and/or polymer material acted upon by a single BFS (or other) mold or die. According to some embodiments, the cap connectors 450 may be configured to be easily removed from the safety cap bodies 446a-g such as by incorporating perforations, stress points, and/or break points that are designed to shear, tear, or sever in response to certain applied forces. The first safety cap 444a may be separated from an adjacent second safety cap 444b, for example, in response to a rotational or twisting force being applied to the joint or juncture where a cap connector 450 is coupled to the first safety cap body 446a (and/or a second safety cap body 446b). In some embodiments, a designed stress or break point may be disposed at the juncture with the safety cap bodies 446a-g, in the middle of a length of the cap connectors 450, or as is or becomes desirable and/or practicable. In such a manner, for example, the safety cap manifold 442 may be quickly and easily manufactured as a single part while allowing the individual safety caps 444a-g to be selectively removed with minimal effort, as is known in the plastic manufacturing arts.

According to some embodiments, fewer or more components 444a-g, 444a-1, 444a-2, 444a-3, 444a-4, 446a-g, 446a-1, 446a-2, 446a-3, 446a-4, 450 and/or various configurations of the depicted components 444a-g, 444a-1, 444a-2, 444a-3, 444a-4, 446a-g, 446a-1, 446a-2, 446a-3, 446a-4, 450 may be included in the safety cap manifold 442 without deviating from the scope of embodiments described herein. In some embodiments, the components 444a-g, 444a-1, 444a-2, 444a-3, 444a-4, 446a-g, 446a-1, 446a-2, 446*a*-3, 446*a*-4, 450 may be similar in configuration and/or functionality to similarly named and/or numbered components as described herein. In some embodiments, the safety cap manifold 442 (and/or portion and/or component 444*a*-*g*, 444*a*-1, 444*a*-2, 444*a*-3, 444*a*-4, 446*a*-*g*, 446*a*-1, 446*a*-2, 446*a*-3, 446*a*-4, 450 thereof) may be utilized in accordance with the methods 900 of FIG. 9 herein, and/or portions thereof.

Figure 5A:
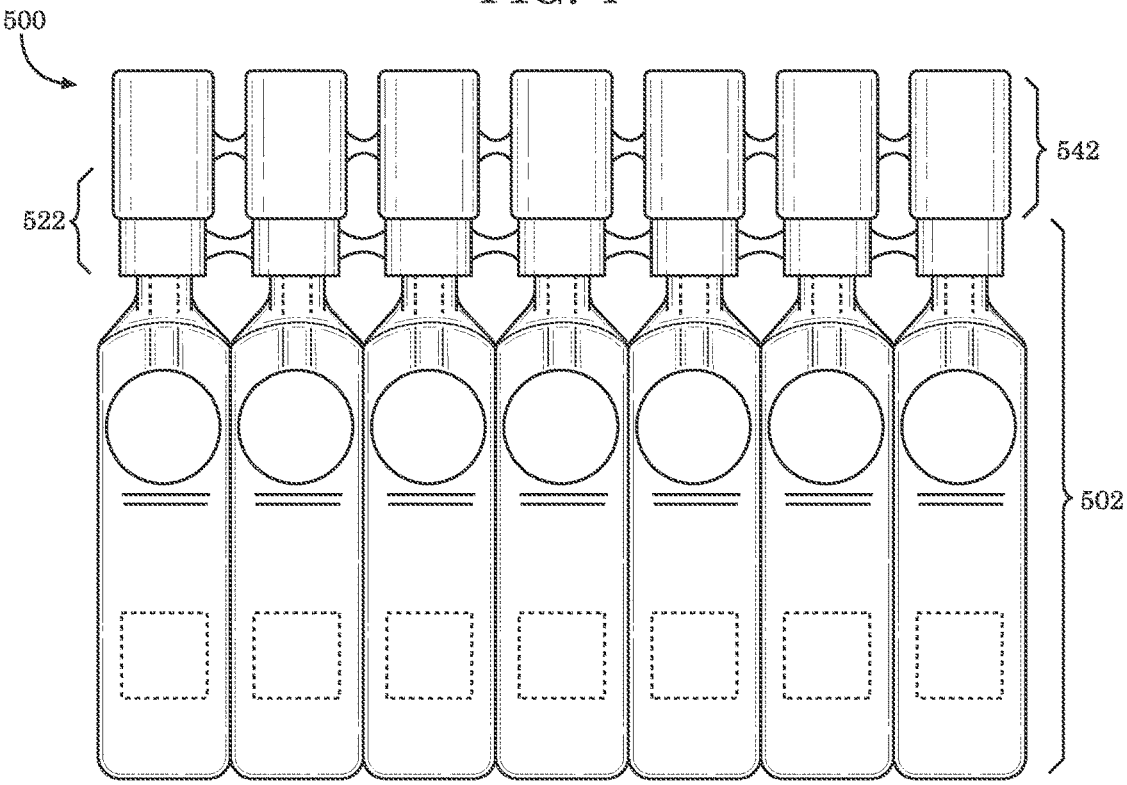
FIG. 5A and FIG. 5B are front and cross-sectional views of a fluid delivery manifold system according to some embodiments.
Figure 5B:
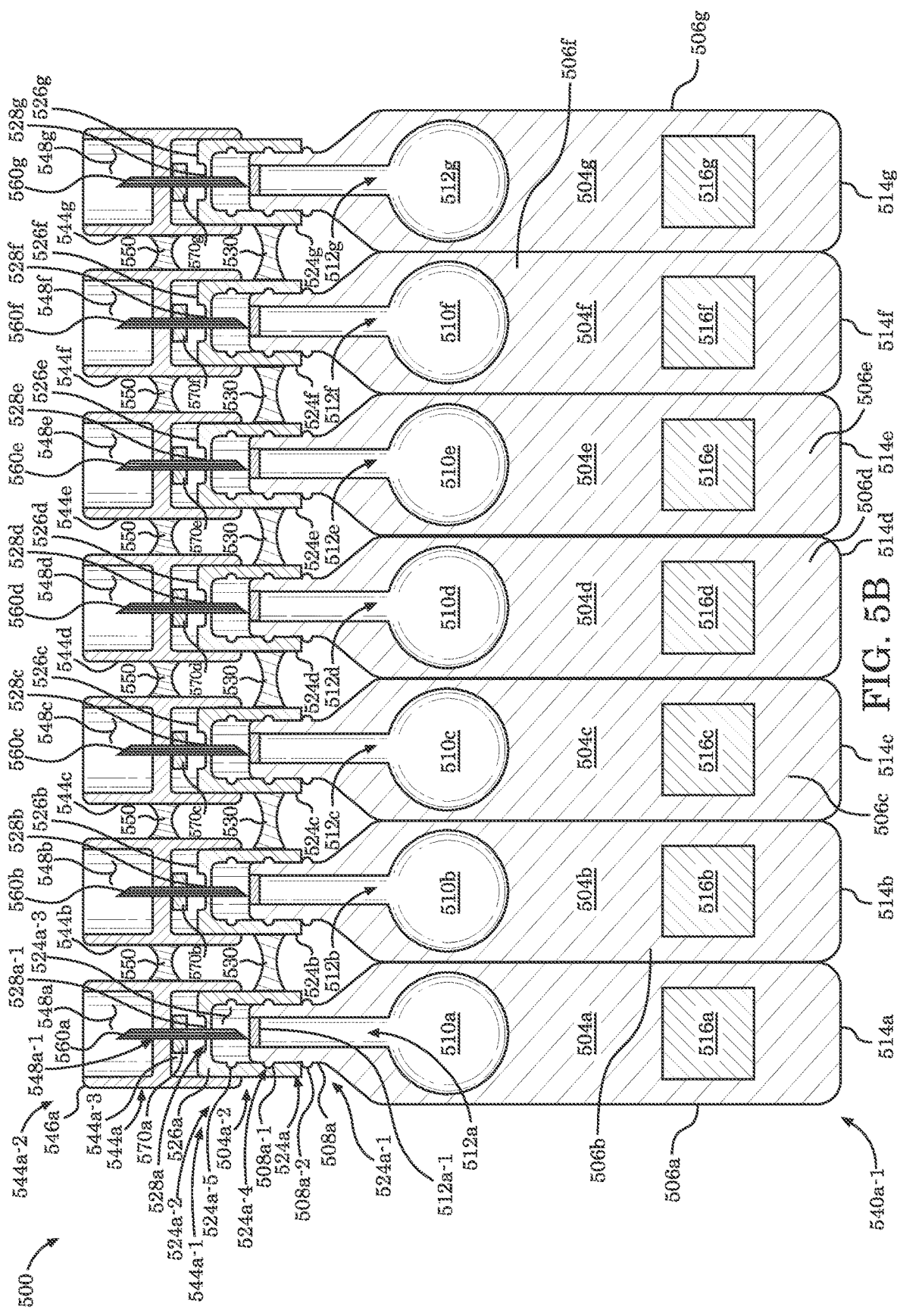
Figures 6A, 6B, 6C:
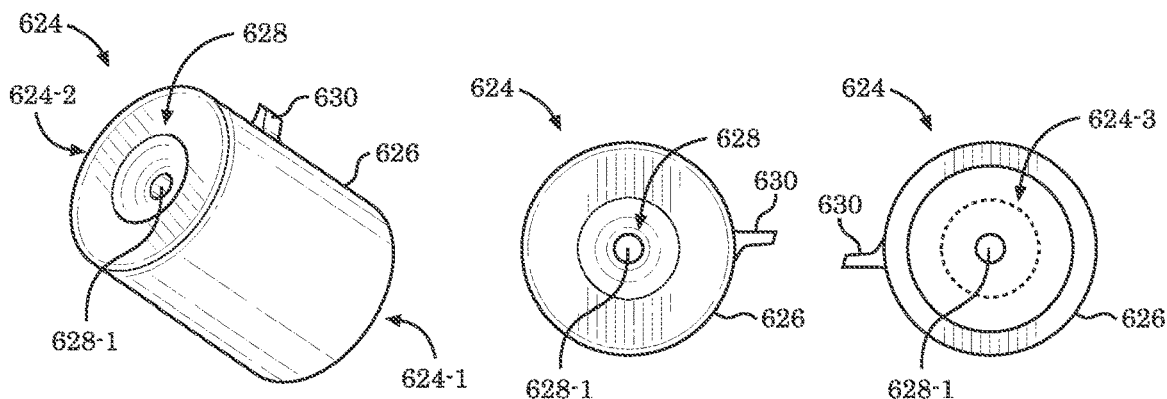
FIG. 6A, FIG. 6B, FIG. 6C, FIG. 6D, FIG. 6E, FIG. 6F, FIG. 6G, and FIG. 6H are top-front perspective, top, bottom, left, right, front, back, and cross-sectional views of a fluid delivery hub according to some embodiments.
Figures 6D, 6E:
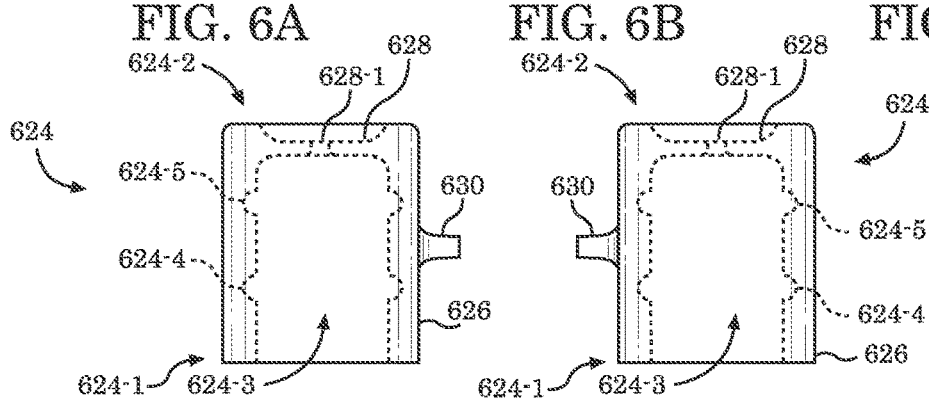
Figures 6F, 6G:
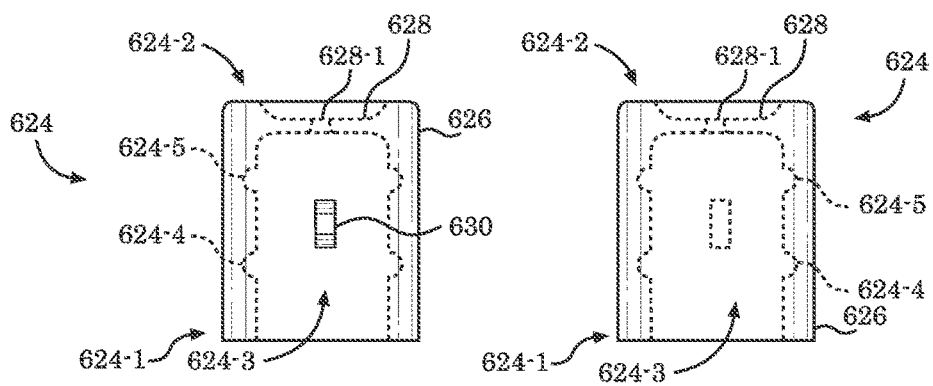
Figure 6H:
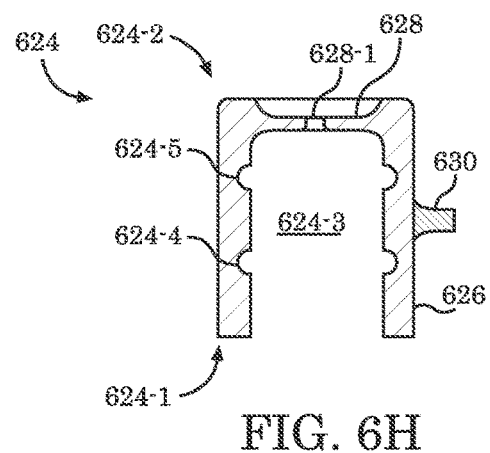

Turning now to FIG. 5A and FIG. 5B, front and cross-sectional views of a fluid delivery manifold system 500 according to some embodiments are shown. The fluid delivery manifold system 500 may comprise, for example, a BFS vial package 502 comprising a plurality if individual BFS vials 504*a*-*g*. Features of the BFS vials 504*a*-*g* are described in representative detail by referring to a first one of the BFS vials 504*a* (e.g., the left-most BFS vial 504*a*-*g* of the BFS vial package 502). According to some embodiments, the first BFS vial 504*a* may comprise a first or proximate end 504*a*-1 and a second or distal end 504*a*-2 between which is disposed a first vial body 506*a*. In some embodiments, each BFS vials 504*a*-*g* may comprise a vial body 506*a*-*g* that may be coupled to any adjacent vial body 506*a*-*g* in the BFS vial package 502 and/or may be coupled to and/or define various features. With reference to the first BFS vial 504*a*, for example, the first vial body 506*a* may comprise, define, and/or be coupled to a first vial neck 508*a* having a first or distal radial flange 508*a*-1 and/or a second or proximate radial flange 508*a*-2 formed and/or coupled thereto.

According to some embodiments, each BFS vial 504*a*-*g* may comprise a fluid reservoir 510*a*-*g* in communication with a respective fluid passage 512*a*-*g* (e.g., a first fluid passage 512*a* of the first BFS vial 504*a* being disposed in (or formed by) the first vial neck 508*a*). With reference to the first BFS vial 504*a*, for example, fluid may be stored in (e.g., injected into during an aseptic BFS manufacturing process) a first fluid reservoir 510*a* and/or the first fluid passage 512*a* an may be prevented from existing the first BFS vial 504*a* by a first fluid seal 512*a*-1 disposed at a distal end of the fluid passage 512*a*. In some embodiments, the BFS vials 504*a*-*g* may comprise grip portions 514*a*-*g* and/or electronic devices 516*a*-*g* (e.g., embedded and/or formed within the BFS vials 504*a*-*g*).

In some embodiments, the fluid delivery manifold system 500 may comprise a fluid delivery manifold 522 coupled to the BFS vial package 502. The fluid delivery manifold 522 may comprise, for example, a plurality of fluid delivery hubs 524*a*-*g*, each fluid delivery hub 524*a*-*g* being coupled to a respective one of the BFS vials 504*a*-*g*. Features of the fluid delivery hubs 524*a*-*g* are described in representative detail by referring to a first one of the fluid delivery hubs 524*a* (e.g., the left-most fluid delivery hub 524*a*-*g* of the fluid delivery manifold 522). The first fluid delivery hub 524*a* may comprise, according to some embodiments, a first or proximate end 524*a*-1 and a second or distal end 524*a*-2 and/or may comprise and/or define a first interior volume 524*a*-3. In some embodiments, the first interior volume 524*a*-3 may comprise one or more internal mating features such as a first or proximate radial channel 524*a*-4 and/or a second or distal radial channel 524*a*-5. According to some embodiments, the fluid delivery hubs 524*a*-*g* may comprise hub bodies 526*a*-*g*, e.g., a first hub body 526*a* of the first fluid delivery hub 524*a* being disposed between the first and second ends 524*a*-1, 524*a*-2 thereof. In some embodiments, the hub bodies 526*a*-*g* may be substantially cylindrical.

As shown in the cross-section of FIG. 5B, the first vial neck 508*a* may be inserted into the first interior volume 524*a*-3 by an amount that aligns first radial flange 508*a*-1 with the proximate radial channel 524*a*-4. In some embodiments, engagement and/or insertion of the first vial neck 508*a* into the first interior volume 524*a*-3 may cause the first vial neck 508*a* of the first BFS vial 504*a* (and/or the first radial flange 508*a*-1 thereof) to compress radially inward and/or may cause the first hub body 526*a* to expand radially outward (e.g., elastically), to allow continued advancement of the first BFS vial 504*a* into the first interior volume 524*a*-3, e.g., in accordance with a tight fit and/or interference fit engagement. According to some embodiments, the radial pressure exerted by forcing the first vial neck 508*a* of the first BFS vial 504*a* into the first interior volume 524*a*-3 may impart a radial spring effect to the first radial flange 508*a*-1 (or a portion thereof) such that when axial advancement aligns the first radial flange 508*a*-1 with the corresponding proximate radial channel 524*a*-4, the first radial flange 508*a*-1 (or a portion thereof) may spring radially outward and into the corresponding proximate radial channel 524*a*-4, thereby reducing and/or removing the radial pressure exerted thereon by the difference between an diameter of the first interior volume 524*a*-3 and an outside diameter and/or radial extents of the first radial flange 508*a*-1. In such a manner, for example, each BFS vial 504*a*-*g* may be snapped into each respective fluid delivery hub 524*a*-*g*.

According to some embodiments, the hub bodies 526*a*-*g* may comprise and/or define seats 528*a*-*g*. As depicted in FIG. 5B, for example, the first hub body 526*a* may comprise a first seat 528*a* disposed or formed on an upper surface at the distal end 524*a*-2 of the first hub body 526*a*. In some embodiments, the first seat 528*a* may be in communication with the first interior volume 524*a*-3 via a bore 528*a*-1 disposed therebetween. In some embodiments, the hub bodies 526*a*-*g* may be joined together to adjacent hub bodies 526*a*-*g* via one or more hub connectors 530. In such a manner, for example, the fluid delivery manifold 522 may be mated with or coupled to the BFS vial package 502 (e.g., as part of a manufacturing assembly process).

In some embodiments, the fluid delivery manifold system 500 may comprise a safety cap manifold 542 coupled to the fluid delivery manifold 522. The safety cap manifold 542 may comprise, for example, a plurality of safety caps 544*a*-*g*, each safety cap 544*a*-*g* being coupled to a respective one of the fluid delivery hubs 524*a*-*g*. Features of the safety caps 544*a*-*g* are described in representative detail by referring to a first one of the safety caps 544*a* (e.g., the left-most safety cap 544*a*-*g* of the safety cap manifold 542). The first safety cap 544*a* may comprise, according to some embodiments, a first or proximate end 544*a*-1 and a second or distal end 544*a*-2 and/or may comprise and/or define a lower void 544*a*-3, e.g., open at the proximate end 544*a*-1. In some embodiments, the lower void 544*a*-3 may comprise one or more internal mating features (not shown) such as to mate to corresponding features (also not shown) on an outside surface of the first fluid delivery hub 524*a* to which the first safety cap 544*a* is coupled.

According to some embodiments, the first safety cap 544*a* may comprise a first cap body 546*a* disposed between the first and second ends 544*a*-1, 544*a*-2 thereof. In some embodiments, the first cap body 546*a* may be substantially cylindrical. In some embodiments, the safety caps 544*a*-*g* may comprise and/or define upper voids 548*a*-*g*. The first safety cap 544*a* may comprise a first upper void 548*a* open at the distal end 544*a*-2, for example, and/or in communication with the first lower void 544*a*-3, e.g., via a first passage 548*a*-1. In some embodiments, the cap bodies 546*a*-*g* may be joined together to adjacent cap bodies 546*a-g* via one or more cap connectors 550. In such a manner, for example, the safety cap manifold 542 may be mated with or coupled to the fluid delivery manifold 522 (e.g., as part of a manufacturing assembly process).

In some embodiments, the mated safety caps 544*a-g* and fluid delivery hubs 524*a-g* may house and/or retain needles or administration members 560*a-g* (e.g., for at least one of subcutaneous, intramuscular, intradermal, and intravenous injection) and/or seals 570*a-g*. As shown with respect to the first BFS vial 504*a*, the first fluid delivery hub 524*a*, and the first safety cap 544*a* coupling, for example, a first administration member 560*a* may extend from within the interior volume 524*a*-3 (e.g., proximate to the first fluid seal 512*a*-1) of the first fluid delivery hub 524*a*, through the bore 528*a*-1 and the first seat 528*a* and into the lower void 544*a*-3 of the first safety cap 544*a*. According to some embodiments, within the lower void 544*a*-3 of the first safety cap 544*a* the first administration member 560*a* may pass through and/or be coupled to a first seal 570 (e.g., an annular rubber seal) and pass through the passage 548*a*-1 of the first safety cap 544*a* and into the first upper void 548*a* thereof. In some embodiments, the upper void 548*a* may be closed at the distal end 544*a*-2, e.g., to prevent accidental access to the first administration member 560*a*. According to some embodiments, the axial length of the first safety cap 544*a* and/or the axial depth or extent of the first upper void 548*a* may be substantially longer than the length of the first administration member 560*a* exposed in the first upper void 548*a* and/or the upper void 548*a* may otherwise not need to be closed at the distal end 544*a*-2.

According to some embodiments, any coupled set of BFS vials 504*a-g*, fluid delivery hubs 524*a-g*, and safety caps 544*a-g* may be configured to be easily removed from the fluid delivery manifold system 500 such as by incorporating perforations, stress points, and/or break points that are designed to shear, tear, or sever in response to certain applied forces. Rotational or twisting force applied to the coupled first BFS vial 504*a*, first fluid delivery hub 524*a*, and first safety cap 544*a* may, for example, generate stresses (i) along a coupling between the first vial body 506*a* and an adjacent second vial body 506*b*, (ii) within the hub connector 530 connecting the first fluid delivery hub 524*a* and an adjacent second delivery hub 524*b*, and/or (iii) within the cap connector 550 connecting the first safety cap 544*a* and an adjacent second safety cap 544*b*. Reduced cross-sectional area at one or more of these various connections may be designed to fail in response to experiencing such stresses, thereby permitting a single-dose BFS vial 504*a-g*, fluid delivery hub 542*a-g*, and safety cap 544*a-g* unit to be easily and selectively removed from the fluid delivery manifold system 500.

While a certain style of safety cap 544*a-g* is depicted in FIG. 5A and FIG. 5B, it should be understood that different styles and/or configurations of safety caps 544*a-g* (e.g., as described herein) may be utilized without deviating from the scope of some embodiments. According to some embodiments, the fluid delivery manifold system 500 may be depicted in FIG. 5A and FIG. 5B in a first, assembled, and/or non-activated state. As depicted, for example, the administration members 560*a-g* have not yet been engaged to puncture the BFS vials 504*a-g* to permit release and/or administration of the fluid stored in the fluid reservoirs 510*a-g*. In some embodiments, an axial compressive force may be applied to the safety caps 544*a-g* and/or the fluid delivery hubs 524*a-g* in one direction and the grip portions 514*a-g* in an opposite direction, to urge the BFS vials 504*a-g* further into the fluid delivery hubs 524*a-g* and cause the administration members 560*a-g* to pierce the respective BFS vials 504*a-g*. In some embodiments, such an activation may be accomplished for single BFS vial 504*a-g* at a time or activation may be effectuated for multiple BFS vials 504*a-g* at one time, e.g., as permitted by the structural configurations, alignment, and engagement of the BFS vial package 502, the fluid delivery manifold 522, and the safety cap manifold 542.

In some embodiments, fewer or more components 502, 504*a-g*, 504*a*-1, 504*a*-2, 506*a-g*, 508*a*, 508*a*-1, 508*a*-2, 510*a-g*, 512*a-g*, 514*a-g*, 516*a-g*, 522, 524*a-g*, 524*a*-1, 524*a*-2, 524*a*-3, 524*a*-4, 524*a*-5, 526*a-g*, 528*a-g*, 528*a*-1, 530, 542, 544*a-g*, 544*a*-1, 544*a*-2, 544*a*-3, 546*a*, 548*a-g*, 548*a*-1, 550, 560*a-g*, 570*a-g* and/or various configurations of the depicted components 502, 504*a-g*, 504*a*-1, 504*a*-2, 506*a-g*, 508*a*, 508*a*-1, 508*a*-2, 510*a-g*, 512*a-g*, 514*a-g*, 516*a-g*, 522, 524*a-g*, 524*a*-1, 524*a*-2, 524*a*-3, 524*a*-4, 524*a*-5, 526*a-g*, 528*a-g*, 528*a*-1, 530, 542, 544*a-g*, 544*a*-1, 544*a*-2, 544*a*-3, 546*a*, 548*a-g*, 548*a*-1, 550, 560*a-g*, 570*a-g* may be included in the fluid delivery manifold system 500 without deviating from the scope of embodiments described herein. In some embodiments, the components 502, 504*a-g*, 504*a*-1, 504*a*-2, 506*a-g*, 508*a*, 508*a*-1, 508*a*-2, 510*a-g*, 512*a-g*, 514*a-g*, 516*a-g*, 522, 524*a-g*, 524*a*-1, 524*a*-2, 524*a*-3, 524*a*-4, 524*a*-5, 526*a-g*, 528*a-g*, 528*a*-1, 530, 542, 544*a-g*, 544*a*-1, 544*a*-2, 544*a*-3, 546*a*, 548*a-g*, 548*a*-1, 550, 560*a-g*, 570*a-g* may be similar in configuration and/or functionality to similarly named and/or numbered components as described herein. In some embodiments, the fluid delivery manifold system 500 (and/or portion and/or component 502, 504*a-g*, 504*a*-1, 504*a*-2, 506*a-g*, 508*a*, 508*a*-1, 508*a*-2, 510*a-g*, 512*a-g*, 514*a-g*, 516*a-g*, 522, 524*a-g*, 524*a*-1, 524*a*-2, 524*a*-3, 524*a*-4, 524*a*-5, 526*a-g*, 528*a-g*, 528*a*-1, 530, 542, 544*a-g*, 544*a*-1, 544*a*-2, 544*a*-3, 546*a*, 548*a-g*, 548*a*-1, 550, 560*a-g*, 570*a-g* thereof) may be utilized in accordance with the method 900 of FIG. 9 herein, and/or portions thereof.

Turning now to FIG. 6A, FIG. 6B, FIG. 6C, FIG. 6D, FIG. 6E, FIG. 6F, FIG. 6G, and FIG. 6H, top-front perspective, top, bottom, left, right, front, back, and cross-sectional views of a fluid delivery hub 624 according to some embodiments are shown. The fluid delivery hub 624 may comprise, for example, a first or proximate end 624-1 and a second or distal end 624-2 and/or may define an interior volume 624-3 (e.g., open at the proximate end 624-1). In some embodiments, the interior volume 624-3 may comprise and/or define one or more mating features (e.g., on an inside surface of the fluid delivery hub 624) such as a first or proximate radial channel 624-4 and/or a second or distal radial channel 624-5. According to some embodiments, the channels 624-4, 624-5 may be beveled and/or rounded, as shown, to facilitate entry and exit of corresponding mating flanges (not shown) thereof. In some embodiments, a lower edge of one or more of the channels 624-4, 624-5 may comprise a right-angle or other angular profile (not shown) such that a corresponding mating feature may readily enter the channel 624-4, 624-5 from the proximate end 624-1 but may be impeded from exiting the channel 624-4, 624-5 (e.g., from backing out) toward the proximate end 624-1. In such a manner, for example, a BFS vial (not shown) with a corresponding mating feature(s) may be easily inserted into the interior volume 624-3 but may be locked therein once engaged, e.g., to prevent attempted reuse of the fluid delivery hub 624.

According to some embodiments, the interior volume 624-3 may be defined by a hub body 626 such as a cylindrical shape as-depicted. In some embodiments, the fluid delivery hub 624 (and/or the hub body 626 thereof) may comprise and/or define a seat 628. The seat 628 may comprise, for example, a depression, indent, and/or countersink feature disposed on a top surface of the hub body 626 at the distal end 624-2. In some embodiments, the seat 628 may comprise a void or volume that is in communication with the interior volume 624-3 via a bore 628-1. According to some embodiments, the fluid delivery hub 624 (and/or the hub body 626 thereof) may comprise a hub connector 630 that may, for example, comprise an element molded and/or coupled to the hub body 626 and operable to be coupled to an adjacent fluid delivery hub (not shown). In some embodiments, the hub connector 630 may comprise a portion of a connective element that connected the hub body 626 to and adjacent hub body and then was selectively severed to remove the fluid delivery hub 624, e.g., from a fluid delivery manifold (not shown) such as the fluid delivery manifolds 222, 522, of FIG. 2, FIG. 5A, and/or FIG. 5B herein.

In some embodiments, fewer or more components 624-1, 624-2, 624-3, 624-4, 624-5, 626, 628, 628-1, 630 and/or various configurations of the depicted components 624-1, 624-2, 624-3, 624-4, 624-5, 626, 628, 628-1, 630 may be included in the fluid delivery hub 624 without deviating from the scope of embodiments described herein. In some embodiments, the components 624-1, 624-2, 624-3, 624-4, 624-5, 626, 628, 628-1, 630 may be similar in configuration and/or functionality to similarly named and/or numbered components as described herein. In some embodiments, the fluid delivery hub 624 (and/or portion and/or component 624-1, 624-2, 624-3, 624-4, 624-5, 626, 628, 628-1, 630 thereof) may be utilized in accordance with the method 900 of FIG. 9 herein, and/or portions thereof.

Figure 7A:
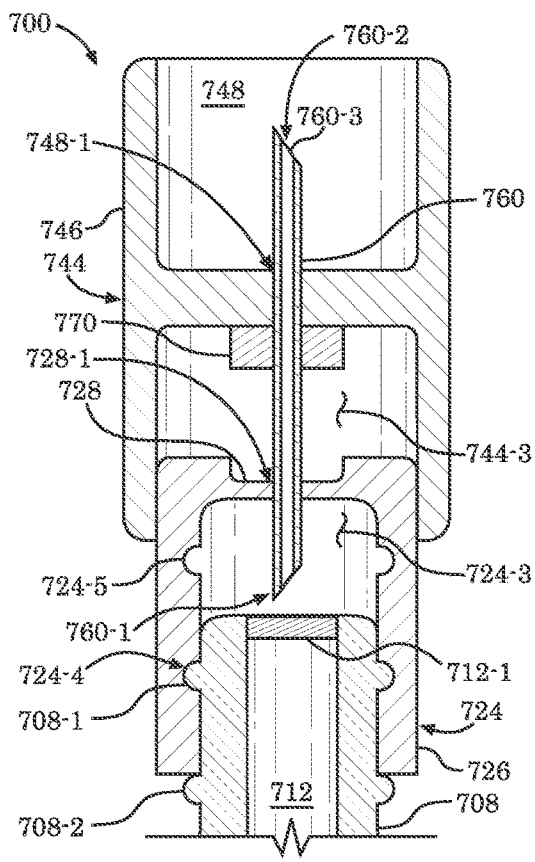
FIG. 7A and FIG. 7B are cross-sectional views of a fluid delivery manifold system according to some embodiments.
Figure 7B:
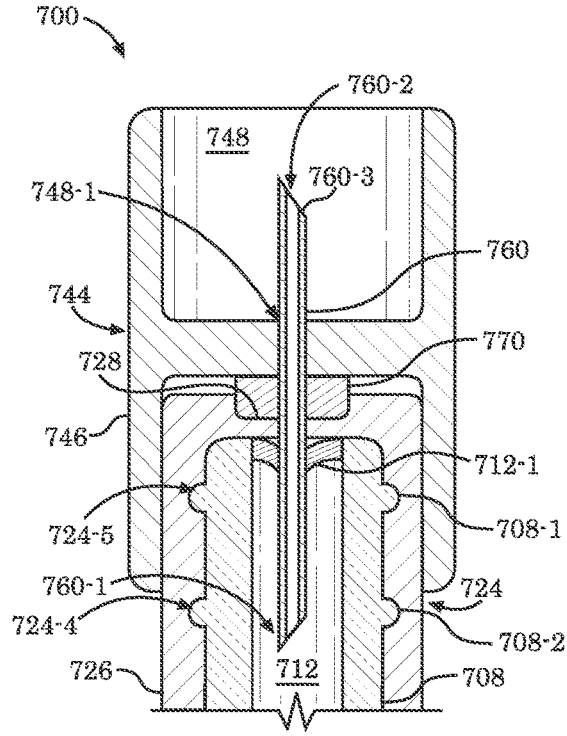

Turning now to FIG. 7A and FIG. 7B, cross-sectional views of a fluid delivery manifold system 700 according to some embodiments are shown. In some embodiments, the fluid delivery manifold system 700 may be depicted in various states of activation in FIG. 7A and FIG. 7B. In FIG. 7A, for example, the fluid delivery manifold system 700 may be depicted in a first or unengaged state while in FIG. 7B the fluid delivery manifold system 700 may be depicted in a second or engaged state. According to some embodiments, a user (not shown) may progress the fluid delivery manifold system 700 from the first state to the second state by selective application of axial force that ultimately causes a fluid to be delivered to a recipient (not shown; e.g., a therapeutic and/or medical fluid to be delivered to a patient).

According to some embodiments, the fluid delivery manifold system 700 may comprise a BFS vial neck 708 having a first or distal exterior radial flange 708-1 and a second or proximate exterior radial flange 708-2. In some embodiments, a fluid (not explicitly shown) may reside in and/or travel through a fluid passage 712 within the BFS vial neck 708 and/or may be contained by a fluid seal 712-1. The fluid seal 712-1 may be integral to the BFS vial neck 708 such as by being formed during a BFS manufacturing process together with the BFS vial neck 708 or may comprise a separate element coupled to seal the BFS vial neck 708 and attendant fluid passage 712 thereof.

In some embodiments, the fluid delivery manifold system 700 may comprise a fluid delivery hub 724 coupled to the BFS vial neck 708. The BFS vial neck 708 may, for example, be at least partially inserted into an interior volume 724-3 defined by the fluid delivery hub 724, e.g., as shown in FIG. 7A. According to some embodiments, the BFS vial neck 708 may have been inserted to a first position within the interior volume 724-3 as shown in FIG. 7A, such that the first radial flange 708-1 engages with and/or becomes seated in a first or proximate radial channel 724-4 disposed on an inside surface of the interior volume 724-3. As depicted in FIG. 7B, continued advancement of the BFS vial neck 708 into the interior volume 724-3 may cause the first radial flange 708-1 to disengage with and/or move out of the first radial channel 724-4 and travel along the inside surface of the interior volume 724-3 until it becomes engaged with and/or seated in a second or distal radial channel 724-5 (as shown in FIG. 7B). Upon achieving such a second and/or additional level of insertion into the interior volume 724-3, in some embodiments the second radial flange 708-2 may become engaged with and/or seated in the first radial channel 724-4 (also as shown in FIG. 7B). In such a manner, for example, at the first state shown in FIG. 7A the BFS vial neck 708 may be secured to the fluid delivery hub 724 at a first position (e.g., via engagement of the first radial flange 708-1 with the first radial channel 724-4; e.g., a transport, assembly, and/or pre-engagement position) while at the second state shown in FIG. 7B the BFS vial neck 708 may be secured to the fluid delivery hub 724 at a second position (e.g., via engagement of the first radial flange 708-1 with the second radial channel 724-5 and engagement of the second radial flange 708-2 with the first radial channel 724-4; e.g., an engagement position). In some embodiments, the interior volume 724-3 (and/or the channels 724-4, 724-5 thereof) may be formed and/or defined by a hub body 726. According to some embodiments, the hub body 726 may comprise and/or define a seat 728 disposed opposite to the interior volume 724-3 and/or a bore 728-1 extending between the seat 728 and the interior volume 724-3.

In some embodiments, the fluid delivery manifold system 700 may comprise a safety cap 744 defining a lower void 744-3 into which the hub body 726 is at least partially inserted and/or disposed (e.g., as shown in FIG. 7A). The lower void 744-3 may comprise an inside diameter equivalent to (or slightly smaller than) an outside diameter of the hub body 726, for example, such as permitting for a desired fit therebetween. According to some embodiments, the lower void 744-3 may be defined by a cap body 746 that may, for example, be cylindrically-shaped. In some embodiments, the safety cap 744 (and/or cap body 746 thereof) may comprise and/or define an upper void 748 in communication with the lower void 744-3 via a passage 748-1.

According to some embodiments, the fluid delivery manifold system 700 may comprise an administration member 760 (such as a needle or tube; e.g., a needle having a length in the ranges of (i) 0.5 mm to 4 mm, (ii) 4 mm to 15 mm, or (iii) 15 mm to 30 mm) having a first or proximate end 760-1 and a second or distal end 760-2. In some embodiments, the administration member 760 may be hollow and/or may otherwise define a fluid channel 760-3 extending from the first end 760-1 to the second end 760-3. In some embodiments, the administration member 760 may pass through and/or be coupled to a seal 770 disposed in the lower void 744-3. The seal 770 may comprise, for example, an annular rubber or thermoplastic element that may be deformable or pliable. According to some embodiments, either or both of the first end 760-1 and the second end 760-2 of the administration member 760 may comprise a tip, point, prong, blade, and/or other feature and/or configuration, such as to pierce the fluid seal 712-1 (e.g., in the case of the fires end 760-1) or pierce an administration surface (such as skin; not shown; e.g., in the case of the second end 760-2).

In some embodiments, and as depicted in FIG. 7A, at the first or disengaged state of the fluid delivery manifold system 700 the first end 760-1 of the administration member 760 may be disposed in the interior volume 724-3 of the fluid delivery hub 724 and the second end 760-2 of the administration member 760 may be disposed in the upper void 748 of the safety cap 744. The administration member 760 may pass through, for example, each of the bore 728-1 (and the seat 728), the seal 770, and the passage 748-1. According to some embodiments, axial force may be applied to transition the fluid delivery manifold system 700 to the second or engaged state of FIG. 7B where the first end 760-1 of the administration member 760 has pierced the fluid seal 712-1 and is disposed within the fluid passage 712 of the BFS vial neck 708 and where the seal 770 is seated in, engaged with, and/or coupled to the seat 728. In such a manner, for example, the fluid delivery manifold system 700 may be engaged to provide the fluid from the fluid passage 712, through the fluid channel 760-3, and into a recipient (not shown). In some embodiments, the safety cap 744 may be removed to expose the administration member 760 and/or the second end 760-2 thereof for administration of the fluid. According to some embodiments, axial force (downward, as-oriented in FIG. 7A and FIG. 7B) may cause the seal 770 to deform and/or compress into the seat 728. Axial force applied to the safety cap 744 may cause the cap body 746 (and/or the ceiling of the interior volume 724-3) to act upon the seal 770 and urge the seal 770 axially downward (e.g., as depicted transitioning from FIG. 7A to FIG. 7B). In some embodiments, once the seal 770 contacts the seat 728 it may be forced therein and/or may be deformed or compressed into the seat 728.

According to some embodiments, upon the seal 770 achieving a degree of compression and/or deformation, force may be transferred to the hub body 726, causing the first radial flange 708-1 of the BFS vial neck 708 to unseat and/or disengage from the first radial channel 724-4, allowing the fluid delivery hub 724 to progress to further envelope the BFS vial neck 708 (e.g., the BFS vial neck 708 advancing further into the interior volume 724-3). In some embodiments, the BFS vial neck 708 may comprise a plastic and/or polymer having a higher degree of compressibility than that of the fluid delivery hub 724, such that the progression of the radial flanges 708-1, 708-2 along the inside walls of the interior volume 724-3 may cause a radially inward compression and/or deformation of the flanges 708-1, 708-2. In some embodiments, such compression may be elastic such that upon encountering an increased interior diameter at the location of either of the channels 724-4, 724-5 the flanges 708-1, 708-2 may spring back radially outward to seat within the channels 724-4, 724-5. According to some embodiments, the seal 770 may be affixed and/or coupled to the administration member 760 such that axial force applied to the seal 770 causes the administration member 760 to move (e.g., as depicted in FIG. 7A and FIG. 7B).

In some embodiments, fewer or more components 708, 708-1, 708-2, 712, 712-1, 724, 724-3, 724-4, 724-5, 726, 728, 728-1, 744, 744-3, 746, 748, 748-1, 760, 760-1, 760-2, 760-3, 770 and/or various configurations of the depicted components 708, 708-1, 708-2, 712, 712-1, 724, 724-3, 724-4, 724-5, 726, 728, 728-1, 744, 744-3, 746, 748, 748-1, 760, 760-1, 760-2, 760-3, 770 may be included in the fluid delivery manifold system 700 without deviating from the scope of embodiments described herein. In some embodiments, the components 708, 708-1, 708-2, 712, 712-1, 724, 724-3, 724-4, 724-5, 726, 728, 728-1, 744, 744-3, 746, 748, 748-1, 760, 760-1, 760-2, 760-3, 770 may be similar in configuration and/or functionality to similarly named and/or numbered components as described herein. In some embodiments, the fluid delivery manifold system 700 (and/or portion and/or component 708, 708-1, 708-2, 712, 712-1, 724, 724-3, 724-4, 724-5, 726, 728, 728-1, 744, 744-3, 746, 748, 748-1, 760, 760-1, 760-2, 760-3, 770 thereof) may be utilized in accordance with the method 900 of FIG. 9 herein, and/or portions thereof.

Figure 8A:
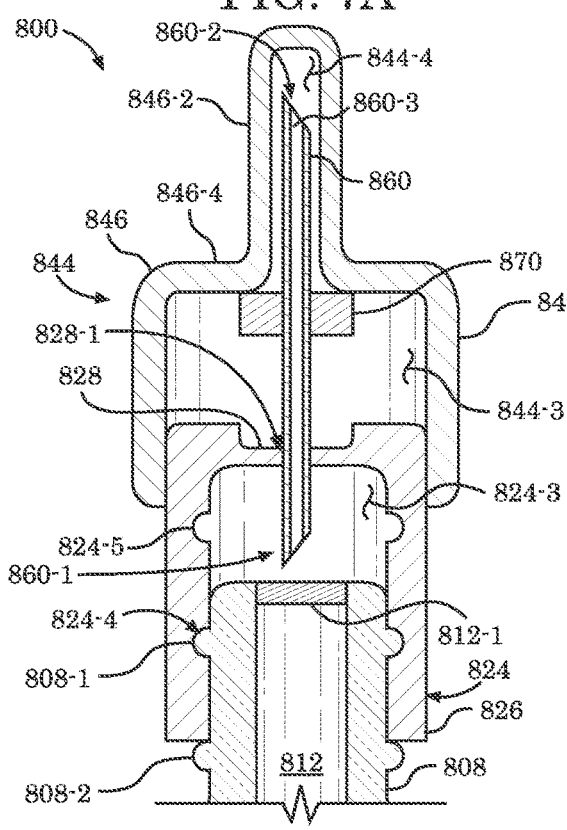
FIG. 8A and FIG. 8B are cross-sectional views of a fluid delivery manifold system according to some embodiments.
Figure 8B:
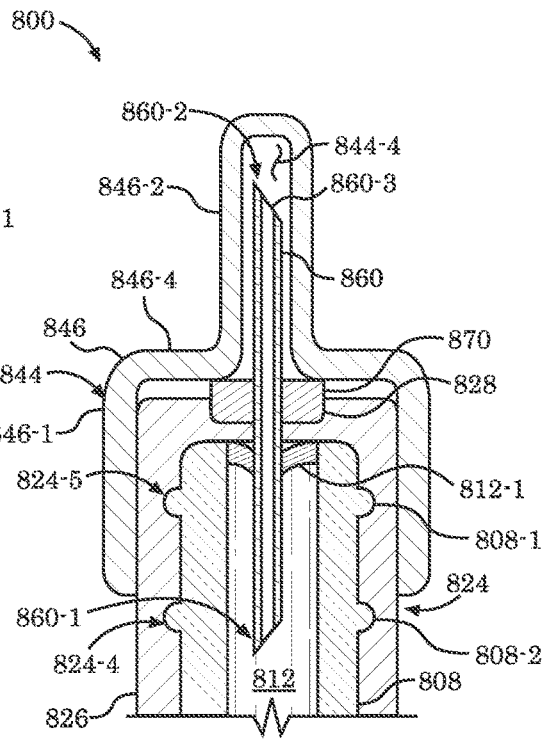

Referring now to FIG. 8A and FIG. 8B, cross-sectional views of a fluid delivery manifold system 800 according to some embodiments are shown. In some embodiments, the fluid delivery manifold system 800 may be depicted in various states of activation in FIG. 8A and FIG. 8B. In FIG. 8A, for example, the fluid delivery manifold system 800 may be depicted in a first or unengaged state while in FIG. 8B the fluid delivery manifold system 800 may be depicted in a second or engaged state. According to some embodiments, a user (not shown) may progress the fluid delivery manifold system 800 from the first state to the second state by selective application of axial force that ultimately causes a fluid to be delivered to a recipient (not shown; e.g., a therapeutic and/or medical fluid to be delivered to a patient).

According to some embodiments, the fluid delivery manifold system 800 may comprise a BFS vial neck 808 having a first or distal exterior radial flange 808-1 and a second or proximate exterior radial flange 808-2. In some embodiments, a fluid (not explicitly shown) may reside in and/or travel through a fluid passage 812 within the BFS vial neck 808 and/or may be contained by a fluid seal 812-1. The fluid seal 812-1 may be integral to the BFS vial neck 808 such as by being formed during a BFS manufacturing process together with the BFS vial neck 808 or may comprise a separate element coupled to seal the BFS vial neck 808 and attendant fluid passage 812 thereof.

In some embodiments, the fluid delivery manifold system 800 may comprise a fluid delivery hub 824 coupled to the BFS vial neck 808. The BFS vial neck 808 may, for example, be at least partially inserted into an interior volume 824-3 defined by the fluid delivery hub 824, e.g., as shown in FIG. 8A. According to some embodiments, the BFS vial neck 808 may have been inserted to a first position within the interior volume 824-3 as shown in FIG. 8A, such that the first radial flange 808-1 engages with and/or becomes seated in a first or proximate radial channel 824-4 disposed on an inside surface of the interior volume 824-3. As depicted in FIG. 8B, continued advancement of the BFS vial neck 808 into the interior volume 824-3 may cause the first radial flange 808-1 to disengage with and/or move out of the first radial channel 824-4 and travel along the inside surface of the interior volume 824-3 until it becomes engaged with and/or seated in a second or distal radial channel 824-5 (as shown in FIG. 8B). Upon achieving such a second and/or additional level of insertion into the interior volume 824-3, in some embodiments the second radial flange 808-2 may become engaged with and/or seated in the first radial channel 824-4 (also as shown in FIG. 8B). In such a manner, for example, at the first state shown in FIG. 8A the BFS vial neck 708 may be secured to the fluid delivery hub 824 at a first position (e.g., via engagement of the first radial flange 808-1 with the first radial channel 824-4; e.g., a transport, assembly, and/or pre-engagement position) while at the second state shown in FIG. 8B the BFS vial neck 808 may be secured to the fluid delivery hub 824 at a second position (e.g., via engagement of the first radial flange 808-1 with the second radial channel 824-5 and engagement of the second radial flange 808-2 with the first radial channel 824-4; e.g., an engagement position). In some embodiments, the interior volume 824-3 (and/or the channels 824-4, 824-5 thereof) may be formed and/or defined by a hub body 826. According to some embodiments, the hub body 826 may comprise and/or define a seat 828 disposed opposite to the interior volume 824-3 and/or a bore 828-1 extending between the seat 828 and the interior volume 824-3.

In some embodiments, the fluid delivery manifold system 800 may comprise a safety cap 844 defining a lower void 844-3 into which the hub body 826 is at least partially inserted and/or disposed (e.g., as shown in FIG. 8A) and/or an upper void 844-4. The lower void 844-3 may comprise an inside diameter equivalent to (or slightly smaller than) an outside diameter of the hub body 826, for example, such as permitting for a desired fit therebetween. According to some embodiments, the lower void 844-3 may be defined by a cap body 846 that may, for example, be comprise a lower body portion 846-1 having a first exterior diameter and an upper body portion 846-2 having a second exterior diameter. According to some embodiments, in the case that the second exterior diameter is smaller than the first exterior diameter, the cap body 846 may comprise and/or define (e.g., at a transition between the lower cap body 846-1 and the upper cap body 846-2) an exterior flange 846-4. In some embodiments, the upper void 844-4 may be defined within the upper body portion 846-2 and the lower void 844-3 may be defined within the lower body portion 846-1.

According to some embodiments, the fluid delivery manifold system 800 may comprise an administration member 860 (such as a needle or tube) having a first or proximate end 860-1 and a second or distal end 860-2. In some embodiments, the administration member 860 may be hollow and/or may otherwise define a fluid channel 860-3 extending from the first end 860-1 to the second end 860-3. In some embodiments, the administration member 860 may pass through and/or be coupled to a seal 870 disposed in the lower void 844-3. The seal 870 may comprise, for example, an annular rubber or thermoplastic element that may be deformable or pliable. According to some embodiments, either or both of the first end 860-1 and the second end 860-2 of the administration member 860 may comprise a tip, point, prong, blade, and/or other feature and/or configuration, such as to pierce the fluid seal 812-1 (e.g., in the case of the fires end 860-1) or pierce an administration surface (such as skin; not shown; e.g., in the case of the second end 860-2).

In some embodiments, and as depicted in FIG. 8A, at the first or disengaged state of the fluid delivery manifold system 800 the first end 860-1 of the administration member 860 may be disposed in the interior volume 824-3 of the fluid delivery hub 824 and the second end 860-2 of the administration member 860 may be disposed in the upper void 848 of the safety cap 844. The administration member 860 may pass through, for example, each of the bore 828-1 (and the seat 828), the seal 870, and the passage 848-1. According to some embodiments, axial force may be applied (e.g., to the exterior flange 846-4) to transition the fluid delivery manifold system 800 to the second or engaged state of FIG. 8B where the first end 860-1 of the administration member 860 has pierced the fluid seal 812-1 and is disposed within the fluid passage 812 of the BFS vial neck 808 and where the seal 870 is seated in, engaged with, and/or coupled to the seat 828. In such a manner, for example, the fluid delivery manifold system 800 may be engaged to provide the fluid from the fluid passage 812, through the fluid channel 860-3, and into a recipient (not shown). In some embodiments, the safety cap 844 may be removed to expose the administration member 860 and/or the second end 860-2 thereof for administration of the fluid. According to some embodiments, axial force (downward, as-oriented in FIG. 8A and FIG. 8B) may cause the seal 870 to deform and/or compress into the seat 828. Axial force applied to the safety cap 844 (e.g., to the exterior flange 846-4 thereof) may cause the cap body 846 (and/or the ceiling of the interior volume 824-3) to act upon the seal 870 and urge the seal 870 axially downward (e.g., as depicted transitioning from FIG. 8A to FIG. 8B). In some embodiments, once the seal 870 contacts the seat 828 it may be forced therein and/or may be deformed or compressed into the seat 828.

According to some embodiments, upon the seal 870 achieving a degree of compression and/or deformation, force may be transferred to the hub body 826, causing the first radial flange 808-1 of the BFS vial neck 808 to unseat and/or disengage from the first radial channel 824-4, allowing the fluid delivery hub 824 to progress to further envelope the BFS vial neck 808 (e.g., the BFS vial neck 808 advancing further into the interior volume 824-3). In some embodiments, the BFS vial neck 808 may comprise a plastic and/or polymer having a higher degree of compressibility than that of the fluid delivery hub 824, such that the progression of the radial flanges 808-1, 808-2 along the inside walls of the interior volume 824-3 may cause a radially inward compression and/or deformation of the flanges 808-1, 808-2. In some embodiments, such compression may be elastic such that upon encountering an increased interior diameter at the location of either of the channels 824-4, 824-5 the flanges 808-1, 808-2 may spring back radially outward to seat within the channels 824-4, 824-5. According to some embodiments, the seal 870 may be affixed and/or coupled to the administration member 860 such that axial force applied to the seal 870 causes the administration member 860 to move (e.g., as depicted in FIG. 8A and FIG. 8B).

In some embodiments, fewer or more components 808, 808-1, 808-2, 812, 812-1, 824, 824-3, 824-4, 824-5, 826, 828, 828-1, 844, 844-3, 844-4, 846, 846-1, 846-2, 846-4, 860, 860-1, 860-2, 860-3, 870 and/or various configurations of the depicted components 808, 808-1, 808-2, 812, 812-1, 824, 824-3, 824-4, 824-5, 826, 828, 828-1, 844, 844-3, 844-4, 846, 846-1, 846-2, 846-4, 860, 860-1, 860-2, 860-3, 870 may be included in the fluid delivery manifold system 800 without deviating from the scope of embodiments described herein. In some embodiments, the components 808, 808-1, 808-2, 812, 812-1, 824, 824-3, 824-4, 824-5, 826, 828, 828-1, 844, 844-3, 844-4, 846, 846-1, 846-2, 846-4, 860, 860-1, 860-2, 860-3, 870 may be similar in configuration and/or functionality to similarly named and/or numbered components as described herein. In some embodiments, the fluid delivery manifold system 800 (and/or portion and/or component 808, 808-1, 808-2, 812, 812-1, 824, 824-3, 824-4, 824-5, 826, 828, 828-1, 844, 844-3, 844-4, 846, 846-1, 846-2, 846-4, 860, 860-1, 860-2, 860-3, 870 thereof) may be utilized in accordance with the method 900 of FIG. 9 herein, and/or portions thereof.

III. Fluid Delivery Manifold Methods

Figure 9:
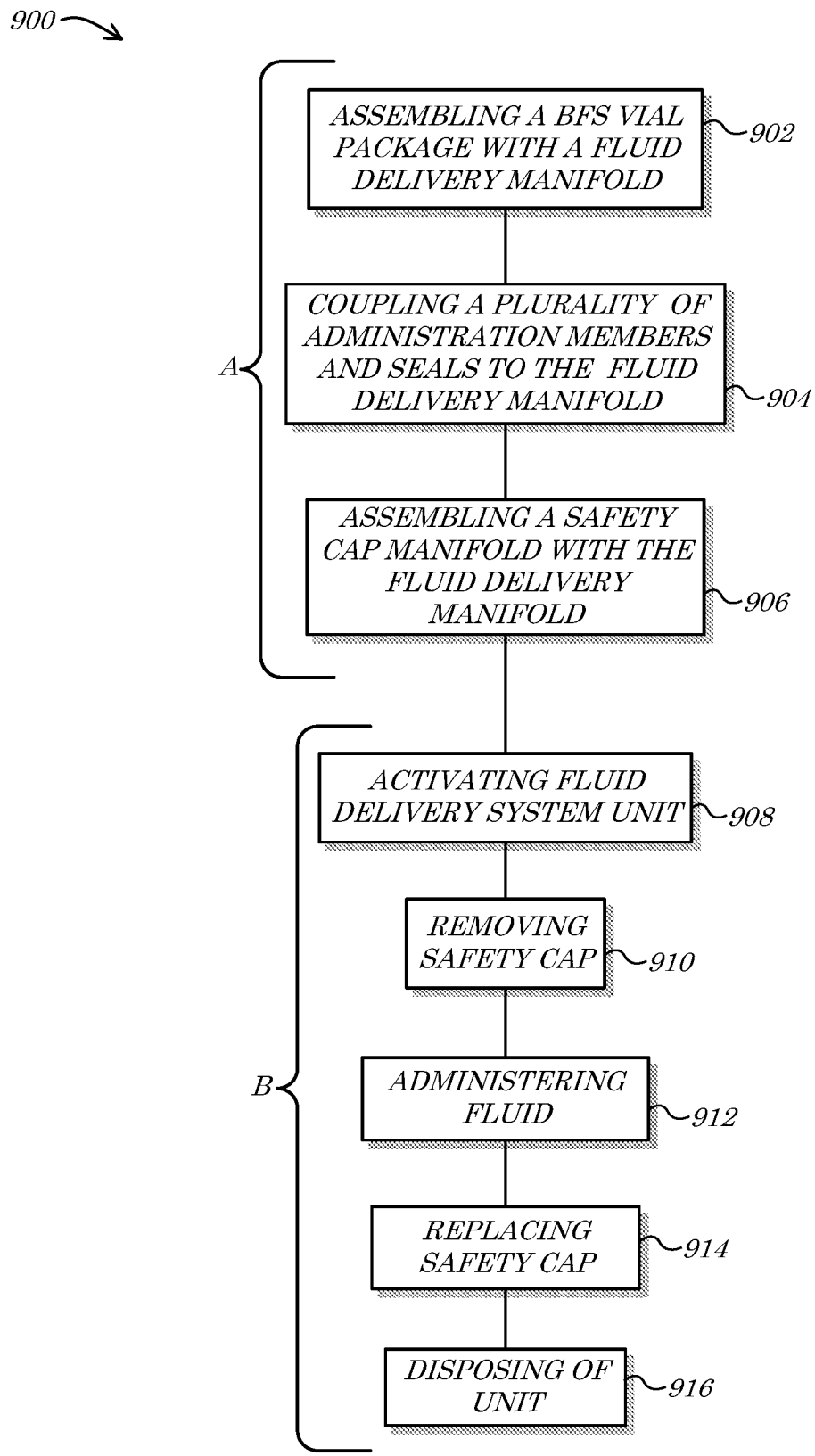
FIG. 9 is a flow diagram of a method according to some embodiments.

FIG. 9 is a flow diagram of a method 900 according to some embodiments. The method 900 may, for example, illustrate an exemplary use of the various fluid delivery manifold systems and/or components thereof, as described herein. In some embodiments, the method 900 may comprise multiple related and/or consecutive processes such as actions associated with a first process "A" and a second process "B". According to some embodiments, the different processes "A", "B" may be performed by different entities and/or at different times and/or locations. The process diagrams and flow diagrams described herein do not necessarily imply a fixed order to any depicted actions, steps, and/or procedures, and embodiments may generally be performed in any order that is practicable unless otherwise and specifically noted. While the order of actions, steps, and/or procedures described herein is generally not fixed, in some embodiments, actions, steps, and/or procedures may be specifically performed in the order listed, depicted, and/or described and/or may be performed in response to any previously listed, depicted, and/or described action, step, and/or procedure.

According to some embodiments, the first process "A" may comprise a manufacturing and/or assembly process. In some embodiments, the first process "A" and/or the method 900 may comprise assembling a BFS vial package with a fluid delivery manifold, at 902. A plurality of BFS vials connected in a package may be mated with corresponding fluid delivery hub members that are also interconnected, for example. According to some embodiments, the assembling may include an aligning of the respective BFS vials (or necks thereof) with individual fluid delivery hub components and applying a first axial force to cause mating of the BFS vials and fluid delivery hubs.

In some embodiments, the method 900 may comprise coupling a plurality of administration members (e.g., needles, droppers, nozzles) and respective fluid seals to the fluid delivery manifold, at 904. Each fluid delivery hub may comprise a bore in which an administration member is inserted, for example. According to some embodiments, the method 900 may comprise assembling a safety cap manifold with the fluid delivery manifold, at 906. In some embodiments, the assembling may include an aligning of the respective fluid delivery hubs with individual safety caps and applying a second axial force to cause mating of the fluid delivery hubs and the safety caps. According to some embodiments, a plurality of interconnected safety caps may be aligned, for example, and engaged with the fluid delivery hubs of the fluid delivery manifold. According to some embodiments, the coupling and/or mating of the safety caps with the fluid delivery hubs may cause the administration members and/or fluid seals to become encapsulated, retained, and/or restricted. In some embodiments, each administration member and each fluid seal may be housed within a respective safety cap and/or between the safety cap and a respective fluid delivery hub. In some embodiments, the assembly and coupling actions may occur in an aseptic environment, such as part of an aseptic BFS manufacturing process that also forms, fills, and seals the BFS vials.

According to some embodiments, the second process "B" may comprise an administration process. In some embodiments, the second process "B" and/or the method 900 may comprise activating a unit of the fluid delivery manifold system, at 908. A third axial force may be applied to axially compress a unit comprising a mated pairing of a BFS vial, a fluid delivery hub, an administration member, a seal, and a safety cap, for example, thereby causing an activation thereof. The third axial force may cause the administration member to pierce a seal of the BFS vial, for example, and/or may cause the fluid seal to become seated and/or coupled to the fluid delivery hub. According to some embodiments, the activating may comprise removing the unit from the respective package and manifolds, such as by application of a twisting, shear, and/or rotational force thereto (e.g., with respect to the other units of the assembled fluid delivery manifold system).

In some embodiments, the method 900 may comprise removing the safety cap of the unit, at 910. Axial separation force may be applied to separate the safety cap from the fluid delivery hub of the unit, for example, exposing the administration member such as a needle, nozzle, dropper, or the like. According to some embodiments, the method 900 may comprise administering a dose of fluid, at 912. The administration element of the unit may be engaged with a patient, for example, and a collapsible and/or integral reservoir of the BFS vial may be squeezed (e.g., via application of inward radial force) to force fluid therefrom. According to some embodiments, the fluid may be forced in an antegrade axial direction such that it displaces a valve flap of a one-way valve, thereby allowing the fluid to proceed axially into the administration element and be delivered to the patient. In some embodiments, the method 900 may comprise replacing the safety cap, at 914. According to some embodiments, the method 900 may comprise disposing of the unit, at 916. In such a manner, for example, a low-cost, easily transported and more easily manufactured, assembled, and stored fluid delivery system may be provided that allows unskilled users to administer and/or self-administer various fluids such as medical and/or therapeutic substances.

IV. Rules of Interpretation

Throughout the description herein and unless otherwise specified, the following terms may include and/or encompass the example meanings provided. These terms and illustrative example meanings are provided to clarify the language selected to describe embodiments both in the specification and in the appended claims, and accordingly, are not intended to be generally limiting. While not generally limiting and while not limiting for all described embodiments, in some embodiments, the terms are specifically limited to the example definitions and/or examples provided. Other terms are defined throughout the present description.

Numerous embodiments are described in this patent application, and are presented for illustrative purposes only. The described embodiments are not, and are not intended to be, limiting in any sense. The presently disclosed invention(s) are widely applicable to numerous embodiments, as is readily apparent from the disclosure. One of ordinary skill in the art will recognize that the disclosed invention(s) may be practiced with various modifications and alterations, such as structural, logical, software, and electrical modifications. Although particular features of the disclosed invention(s) may be described with reference to one or more particular embodiments and/or drawings, it should be understood that such features are not limited to usage in the one or more particular embodiments or drawings with reference to which they are described, unless expressly specified otherwise.

Devices that are in communication with each other need not be in continuous communication with each other, unless expressly specified otherwise.

A description of an embodiment with several components or features does not imply that all or even any of such components and/or features are required. On the contrary, a variety of optional components are described to illustrate the wide variety of possible embodiments of the present invention(s). Unless otherwise specified explicitly, no component and/or feature is essential or required.

Further, although process steps, algorithms or the like may be described in a sequential order, such processes may be configured to work in different orders. In other words, any sequence or order of steps that may be explicitly described does not necessarily indicate a requirement that the steps be performed in that order. The steps of processes described herein may be performed in any order practical. Further, some steps may be performed simultaneously despite being described or implied as occurring non-simultaneously (e.g., because one step is described after the other step). Moreover, the illustration of a process by its depiction in a drawing does not imply that the illustrated process is exclusive of other variations and modifications thereto, does not imply that the illustrated process or any of its steps are necessary to the invention, and does not imply that the illustrated process is preferred.

The present disclosure provides, to one of ordinary skill in the art, an enabling description of several embodiments and/or inventions. Some of these embodiments and/or inventions may not be claimed in the present application, but may nevertheless be claimed in one or more continuing applications that claim the benefit of priority of the present application. Applicants intend to file additional applications to pursue patents for subject matter that has been disclosed and enabled but not claimed in the present application.

It will be understood that various modifications can be made to the embodiments of the present disclosure herein without departing from the scope thereof. Therefore, the above description should not be construed as limiting the disclosure, but merely as embodiments thereof. Those skilled in the art will envision other modifications within the scope of the invention as defined by the claims appended hereto.

While several embodiments of the present disclosure have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present disclosure. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present disclosure is/are used.

Those skilled in the art will recognize, or be able to ascertain using no more than routine experimentation, many equivalents to the specific embodiments of the disclosure described herein. It is, therefore, to be understood that the foregoing embodiments are presented by way of example only and that, within the scope of the appended claims and equivalents thereto, the disclosure may be practiced otherwise than as specifically described and claimed. The present disclosure is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present disclosure.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified, unless clearly indicated to the contrary.

Reference throughout this specification to "one embodiment" or "an embodiment" means that a particular feature, structure, or characteristic described in connection with the embodiment is included in at least one embodiment. Thus, appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

The terms and expressions which have been employed herein are used as terms of description and not of limitation, and there is no intention, in the use of such terms and expressions, of excluding any equivalents of the features shown and described (or portions thereof), and it is recognized that various modifications are possible within the scope of the claims. Accordingly, the claims are intended to cover all such equivalents.

Various modifications of the invention and many further embodiments thereof, in addition to those shown and described herein, will become apparent to those skilled in the art from the full contents of this document, including references to the scientific and patent literature cited herein. The subject matter herein contains important information, exemplification and guidance that can be adapted to the practice of this invention in its various embodiments and equivalents thereof.

What is claimed is:

1. A fluid delivery system for delivery of a fluid agent, the fluid delivery system comprising:
    an individual BFS vial containing a single dose of a fluid agent, the BFS vial comprising a radially compressible reservoir containing the single dose of the fluid agent and comprising a cylindrical neck defining a fluid channel in communication with the radially compressible reservoir and the BFS vial comprising at least one mating feature disposed on an exterior surface thereof;
    a fluid delivery hub defining an interior volume having one or more mating features disposed on an interior surface therein, and each of the one or more mating features being coupled to a corresponding one of the at least one mating feature of the exterior surface of the BFS vial; and
    an administration member being coupled to the fluid delivery hub.

2. The fluid delivery system of claim 1, wherein the administration member comprises a needle for at least one of subcutaneous, intramuscular, intradermal, and intravenous injection of the fluid agent into a recipient.

3. The fluid delivery system of claim 2, wherein the needle comprises a length in the range of 0.5 mm to 4 mm.

4. The fluid delivery system of claim 2, wherein the needle comprises a length in the range of 4 mm to 15 mm.

5. The fluid delivery system of claim 2, wherein the needle comprises a length in the range of 15 mm to 30 mm.

6. The fluid delivery system of claim 1, wherein the BFS vial comprises an electronic device storing data descriptive of the fluid agent.

7. The fluid delivery system of claim 6, wherein the electronic device comprises a Near-Field-Communication (NFC) device.

8. The fluid delivery system of claim 7, wherein the NFC device is operable to facilitate processing of data defining the geographical movement of the BFS vial.

9. The fluid delivery system of claim 7, wherein the NFC device is operable to facilitate processing of data that allows a verification that the BFS vial is authorized for administration to a particular recipient.

10. The fluid delivery system of claim 1, wherein the at least one mating feature disposed on the exterior surface of the BFS vial comprises a radial flange and wherein the one or more mating features disposed on the interior surface of the fluid delivery hub comprises a radial channel.

11. The fluid delivery system of claim 1, wherein the administration member comprises a needle comprising a point on each end thereof.

12. The fluid delivery system of claim 11, wherein the BFS vial comprises a fluid seal that is integral to a terminus of the BFS vial cylindrical neck, and wherein the mating of the BFS vial with the fluid delivery hub positions one of the needle points to pierce the fluid seal of the BFS vial.

13. The fluid delivery system of claim 1, further comprising:
a safety cap coupled to the fluid delivery hub such that it shields a distal point of the administration member.

14. The fluid delivery system of claim 13, wherein axial force applied to the safety cap causes a proximate point of the administration member to pierce a fluid seal formed at a terminus of the cylindrical neck of the BFS vial.

15. A fluid delivery system for delivery of a single dose of a fluid agent, the fluid delivery system comprising:
an individual Blow Fill Seal (BFS) vial containing a single dose of a fluid agent in a fluid reservoir and defining a cylindrical neck in fluid communication with the fluid reservoir and comprising a fluid seal at an end thereof and the BFS vial comprising an exterior flange on an exterior surface thereof;
an annular plastic element retaining an axially-oriented needle comprising a first piercing tip at a first end thereof and a second piercing tip at a second end thereof;
a safety cap defining a lower void in which the annular plastic element and the second piercing tip of the needle are disposed; and
a fluid delivery hub defining an interior volume comprising a seat disposed on an interior surface therein and a passage disposed axially therethrough, the needle being coupled through the passage and the first piercing tip thereof extending into the interior volume such that an axial engagement of the safety cap causes the annular plastic element to exert axial force upon the fluid delivery hub, thereby mating the exterior flange with the seat and causing the first piercing tip of the needle to pierce the fluid seal of the cylindrical neck.

16. The fluid delivery system of claim 15, wherein the needle is configured for at least one of subcutaneous, intramuscular, intradermal, and intravenous injection of the fluid agent into a recipient.

17. The fluid delivery system of claim 16, wherein the needle comprises a length in the range of 0.5 mm to 4 mm.

18. The fluid delivery system of claim 15, wherein the exterior flange comprises a rounded radial flange.

19. The fluid delivery system of claim 15, wherein the seat of the interior volume of the fluid delivery hub comprises a rounded radial channel.

20. The fluid delivery system of claim 19, wherein the seat comprises a first rounded radial channel and the exterior flange comprises a first exterior radial flange, and wherein the BFS vial further comprises a second exterior radial flange and wherein the fluid delivery hub comprises a second rounded radial channel disposed on the interior surface therein, and wherein the fluid seal is integral to a terminus of the BFS vial cylindrical neck, and wherein a mating of the second exterior radial flange with the second rounded radial channel positions the first piercing tip of the needle proximate to, and axially aligned with, the fluid seal of the BFS vial.

* * * * *